(12) United States Patent
Almond et al.

(10) Patent No.: US 8,642,577 B2
(45) Date of Patent: Feb. 4, 2014

(54) COMPOUNDS, COMPOSITIONS AND METHODS FOR THE TREATMENT OF POXVIRUS INFECTIONS

(75) Inventors: Merrick R. Almond, Apex, NC (US); George R. Painter, Chapel Hill, NC (US)

(73) Assignee: Chimerix, Inc., Durham, NC (US)

( * ) Notice: Subject to any disclaimer, the term of this patent is extended or adjusted under 35 U.S.C. 154(b) by 1164 days.

(21) Appl. No.: 11/401,805

(22) Filed: Apr. 10, 2006

(65) Prior Publication Data

US 2007/0003516 A1 Jan. 4, 2007

Related U.S. Application Data

(60) Provisional application No. 60/669,730, filed on Apr. 8, 2005.

(51) Int. Cl.
*A61K 31/675* (2006.01)
*A61K 31/40* (2006.01)

(52) U.S. Cl.
USPC .............................. 514/86; 514/410; 514/411

(58) Field of Classification Search
USPC .......................................................... 514/86
See application file for complete search history.

(56) References Cited

U.S. PATENT DOCUMENTS

| | | | |
|---|---|---|---|
| 1,944,530 A | 1/1934 | Schonburg | |
| 3,422,021 A | 1/1969 | Roy | |
| 3,468,935 A | 9/1969 | Peck | |
| 4,327,039 A | 4/1982 | Blum et al. | |
| 4,444,766 A | 4/1984 | Bosies et al. | |
| 4,562,179 A | 12/1985 | Teraji et al. | |
| 4,619,794 A | 10/1986 | Hauser | |
| 4,705,651 A | 11/1987 | Staibano | |
| 4,870,063 A | 9/1989 | Binderup et al. | |
| 4,927,814 A | 5/1990 | Gall et al. | |
| 5,043,437 A | 8/1991 | Khorlin et al. | |
| 5,047,533 A | 9/1991 | Reist et al. | |

(Continued)

FOREIGN PATENT DOCUMENTS

| | | |
|---|---|---|
| CS | 220713 B1 | 4/1983 |
| EP | 0186405 A2 | 7/1986 |

(Continued)

OTHER PUBLICATIONS

Kern et al. "Enhanced inhibition of orthopoxvirus replication in vitro by alkoxyl ester of cidofovir and cyclic cidofovir," Antimicrobial agents and Chemotherapy, 2002, vol. 46, No. 4, pp. 991-995.*

(Continued)

*Primary Examiner* — Shengjun Wang
(74) *Attorney, Agent, or Firm* — Mintz Levin Cohn Ferris Glovsky and Popeo, P.C.; Ivor R. Elrifi; Heidi A. Erlacher

(57) ABSTRACT

The present application provides methods and compositions for combination therapy with antiviral compounds for the treatment of poxvirus infections, such as orthopox virus infections. In one embodiment, a method of treatment of a poxvirus infection is provided that comprises administering to a host in need thereof cidofovir, cyclic cidofovir, or a salt, ester, or prodrug thereof in combination or alternation with at least a second anti-poxvirus agent. The second anti-poxvirus agent is, for example, a biologic, such as a pegylated interferon.

11 Claims, 2 Drawing Sheets

Monkeypox Titers in Key Tissues

(56) References Cited

U.S. PATENT DOCUMENTS

| | | |
|---|---|---|
| 5,142,051 A | 8/1992 | Holy et al. |
| 5,183,815 A | 2/1993 | Saari et al. |
| 5,194,654 A | 3/1993 | Hostetler et al. |
| 5,196,409 A | 3/1993 | Breuer et al. |
| 5,223,263 A | 6/1993 | Hostetler et al. |
| 5,247,085 A | 9/1993 | Harnden et al. |
| 5,300,671 A | 4/1994 | Tognella et al. |
| 5,300,687 A | 4/1994 | Schwender et al. |
| 5,312,954 A | 5/1994 | Breuer et al. |
| 5,395,826 A | 3/1995 | Naumann et al. |
| 5,411,947 A | 5/1995 | Hostetler et al. |
| 5,428,181 A | 6/1995 | Sugioka et al. |
| 5,442,101 A | 8/1995 | Hanhijarvi et al. |
| 5,463,092 A | 10/1995 | Hostetler et al. |
| 5,476,938 A | 12/1995 | Vemishetti et al. |
| 5,484,809 A | 1/1996 | Hostetler et al. |
| 5,484,911 A | 1/1996 | Hong et al. |
| 5,512,671 A | 4/1996 | Piantadosi et al. |
| 5,532,226 A | 7/1996 | Demarest et al. |
| 5,591,852 A | 1/1997 | Vemishetti et al. |
| 5,614,548 A | 3/1997 | Piantadosi et al. |
| 5,627,185 A | 5/1997 | Gosselin et al. |
| 5,650,510 A | 7/1997 | Webb, II et al. |
| 5,656,745 A | 8/1997 | Bischofberger et al. |
| 5,663,159 A | 9/1997 | Starrett, Jr. et al. |
| 5,672,697 A | 9/1997 | Buhr et al. |
| 5,696,277 A | 12/1997 | Hostetler et al. |
| 5,717,095 A | 2/1998 | Arimilli et al. |
| 5,744,461 A | 4/1998 | Hostetler et al. |
| 5,744,592 A | 4/1998 | Hostetler et al. |
| 5,756,711 A | 5/1998 | Zilch et al. |
| 5,760,013 A | 6/1998 | Hwu et al. |
| 5,770,584 A | 6/1998 | Kucera et al. |
| 5,780,617 A | 7/1998 | van den Bosch et al. |
| 5,792,756 A | 8/1998 | Starrett, Jr. et al. |
| 5,798,340 A | 8/1998 | Bischofberger et al. |
| 5,817,638 A | 10/1998 | Hostetler |
| 5,827,831 A | 10/1998 | Hostetler et al. |
| 5,840,716 A | 11/1998 | Ubasawa et al. |
| 5,854,228 A | 12/1998 | Webb, II et al. |
| 5,856,314 A | 1/1999 | Kaas et al. |
| 5,869,468 A | 2/1999 | Freeman |
| 5,877,166 A | 3/1999 | Reist et al. |
| 5,885,973 A | 3/1999 | Papapoulos et al. |
| 5,886,179 A | 3/1999 | Arimilli et al. |
| 5,922,695 A | 7/1999 | Arimilli et al. |
| 5,922,696 A | 7/1999 | Casara et al. |
| 5,962,437 A | 10/1999 | Kucera et al. |
| 5,977,061 A | 11/1999 | Holy et al. |
| 5,977,089 A | 11/1999 | Arimilli et al. |
| 6,002,029 A | 12/1999 | Hostetler et al. |
| 6,030,960 A | 2/2000 | Morris-Natschke et al. |
| 6,043,230 A | 3/2000 | Arimilli et al. |
| 6,069,249 A | 5/2000 | Arimilli et al. |
| 6,194,388 B1 | 2/2001 | Krieg et al. |
| 6,207,646 B1 | 3/2001 | Krieg et al. |
| 6,218,371 B1 | 4/2001 | Krieg et al. |
| 6,225,292 B1 | 5/2001 | Raz et al. |
| 6,239,116 B1 | 5/2001 | Krieg et al. |
| 6,252,060 B1 | 6/2001 | Hostetler |
| 6,448,392 B1 | 9/2002 | Hostetler et al. |
| 6,562,798 B1 | 5/2003 | Schwartz |
| 6,589,940 B1 | 7/2003 | Raz et al. |
| 6,605,602 B1 | 8/2003 | Vats |
| 6,635,472 B1 | 10/2003 | Lauermann |
| RE38,333 E | 11/2003 | Arimilli et al. |
| 6,670,341 B1 | 12/2003 | Kucera et al. |
| 6,716,825 B2 | 4/2004 | Hostetler et al. |
| 6,818,629 B2 | 11/2004 | Peterson et al. |
| 7,026,469 B2 | 4/2006 | Kucera et al. |
| 7,034,014 B2 | 4/2006 | Hostetler et al. |
| 7,094,772 B2 | 8/2006 | Hostetler et al. |
| 7,098,197 B2 | 8/2006 | Hostetler et al. |
| 7,288,265 B1 | 10/2007 | Rolf |
| 7,390,791 B2 | 6/2008 | Becker et al. |
| 7,452,898 B2 | 11/2008 | Hostetler et al. |
| 7,652,001 B2 | 1/2010 | Hostetler et al. |
| 7,749,983 B2 | 7/2010 | Hostetler et al. |
| 7,790,703 B2 | 9/2010 | Hostetler et al. |
| 2003/0211072 A1 | 11/2003 | Carreno-Gomez et al. |
| 2004/0019232 A1 | 1/2004 | Hostetler et al. |
| 2004/0022873 A1 | 2/2004 | Guilford et al. |
| 2004/0071757 A1 | 4/2004 | Rolf |
| 2004/0161398 A1 | 8/2004 | Kucera et al. |
| 2004/0224917 A1 | 11/2004 | Dahl et al. |
| 2004/0259845 A1 | 12/2004 | Kucera et al. |
| 2005/0187192 A1 | 8/2005 | Fleming et al. |
| 2005/0261237 A1 | 11/2005 | Boojamra et al. |
| 2006/0128692 A1 | 6/2006 | Chen et al. |
| 2006/0263355 A1 | 11/2006 | Quan et al. |
| 2007/0003516 A1 | 1/2007 | Almond et al. |
| 2007/0003608 A1 | 1/2007 | Almond et al. |
| 2007/0026056 A1 | 2/2007 | Rolf |
| 2007/0154454 A1 | 7/2007 | Murphy et al. |
| 2008/0009462 A1 | 1/2008 | Hostetler et al. |
| 2008/0020018 A1 | 1/2008 | Moodley et al. |
| 2008/0161324 A1 | 7/2008 | Johansen et al. |
| 2009/0017448 A1 | 1/2009 | Toth et al. |
| 2009/0087451 A1 | 4/2009 | Buller |
| 2009/0111774 A1 | 4/2009 | Tokars et al. |
| 2009/0181931 A1 | 7/2009 | Urata et al. |
| 2010/0173870 A1 | 7/2010 | Hostetler et al. |

FOREIGN PATENT DOCUMENTS

| | | |
|---|---|---|
| EP | 0253412 A2 | 1/1988 |
| EP | 0632048 A1 | 1/1995 |
| EP | 0753523 A1 | 1/1997 |
| EP | 0897709 A1 | 2/1999 |
| EP | 1438962 A1 | 7/2004 |
| EP | 1914237 A2 | 4/2008 |
| GB | 1280788 A | 7/1972 |
| JP | 61-152694 A2 | 7/1986 |
| JP | 10029998 A | 2/1998 |
| WO | WO-9105558 A1 | 5/1991 |
| WO | WO-9109602 A2 | 7/1991 |
| WO | WO-9520980 A1 | 8/1995 |
| WO | WO 96/02555 A1 | 2/1996 |
| WO | WO-9640088 A1 | 12/1996 |
| WO | WO 97/28259 A1 | 8/1997 |
| WO | WO 98/16247 A1 | 4/1998 |
| WO | WO 98/18810 A1 | 5/1998 |
| WO | WO 98/38202 A1 | 9/1998 |
| WO | WO 98/40100 A1 | 9/1998 |
| WO | WO 98/52581 A1 | 11/1998 |
| WO | WO 98/55495 A2 | 12/1998 |
| WO | WO-9908685 A1 | 2/1999 |
| WO | WO 99/51259 A2 | 10/1999 |
| WO | WO-0004032 A1 | 1/2000 |
| WO | WO 00/06588 A1 | 2/2000 |
| WO | WO 00/21556 A1 | 4/2000 |
| WO | WO-0037477 A1 | 6/2000 |
| WO | WO 01/12223 A2 | 2/2001 |
| WO | WO 01/22972 A1 | 4/2001 |
| WO | WO 01/22990 A2 | 4/2001 |
| WO | WO 01/39724 A2 | 6/2001 |
| WO | WO-03049746 A2 | 6/2003 |
| WO | WO-2004062600 A2 | 7/2004 |
| WO | WO 2004/112718 * | 12/2004 |
| WO | WO-2005087788 A2 | 9/2005 |
| WO | WO-2005121378 A2 | 12/2005 |
| WO | WO-2006066074 A2 | 6/2006 |
| WO | WO-2006076015 A2 | 7/2006 |
| WO | WO-2006110655 A2 | 10/2006 |
| WO | WO-2006110656 A2 | 10/2006 |
| WO | WO-2006130217 A2 | 12/2006 |
| WO | WO-2007130783 A2 | 11/2007 |
| WO | WO-2008033466 A2 | 3/2008 |
| WO | WO-2008118013 A2 | 10/2008 |
| WO | WO-2008133966 A1 | 11/2008 |
| WO | WO-2008133982 A2 | 11/2008 |
| WO | WO-2008144743 A1 | 11/2008 |

(56) References Cited

FOREIGN PATENT DOCUMENTS

| | | |
|---|---|---|
| WO | WO-2011011519 A1 | 1/2011 |
| WO | WO-2011017253 A1 | 2/2011 |
| WO | WO-2011053812 A1 | 5/2011 |

OTHER PUBLICATIONS

Huggins et al. "Cidofovir Treatment of Variola (Smallpox) in the Hemorrhagic Smallpox Primate Model and the IV Monkeypox Primate Model", *Antiviral Research* 57(3):A78 (2003) (Abstract #127).
Huggins et al. "Successful Cidofovir Treatment of Smallpox-Like Disease in Variola and Monkeypox Primate Models", *Antiviral Research* 62(2):A57-A58 (2004) (Abstract #76).
Buller et al. "Efficacy of Smallpox Vaccination in the Presence of Antiviral Drugs, Cidofovir and Hexadecyoxypropylcidofovir", *Antiviral Research* 65(3):A80 (2005) (Abstract #72).
Remichkova et al. "Synergistic Combination Effect of Cidofovir and Idoxuridine on Vaccinia Virus Replication", *Antiviral Research* 65(3):A80-A81 (2005) (Abstract #74).
Notification of the International Search Report and The Written Opinion of the International Searching Authority, or the Declaration corresponding to International Application No. PCT/US06/13319 mailed Apr. 25, 2007.
Bell, E., et al., "Antibodies against the extracellular enveloped virus B5R protein are mainly responsible for the EEV neutralizing capacity of vaccinia immune globulin.," *Virology*, 325(2):425-431 (Aug. 1, 2004).
Blasco, R., and Moss, B., "Extracellular vaccinia virus formation and cell-to-cell virus transmission are prevented by deletion of the gene encoding the 37,000-Dalton outer envelope protein," *J. Virol.*, 65(11):5910-5920 (Nov. 1991).
Bray, M., "Pathogenesis and potential antiviral therapy of complications of smallpox vaccination," *Antiviral Res.*, 58(2):101-114 (Apr. 2003).
Keith, K.A., et al., "Inhibitory activity of alkoxyalkyl and alkyl esters of cidofovir and cyclic cidofovir against orthopoxvirus replication in vitro," *Antimicrob. Agents Chemother.*, 48(5):1869-1871(May 2004).
Komori, M., et al., "Cytochrome P-450 in human liver microsomes: high-performance liquid chroma-tographic isolation of three forms and their characterization," *J. Biochem.* (Tokyo), 104(6):912-916 (Dec. 1988).
Wan, W.B., et al., "Comparison of the antiviral activities of alkoxyalkyl and alkyl esters of cidofovir against human and murine cytomegalovirus replication in vitro,"*Antimicrob. Agents Chemother.*, 49(2):656-662 (Feb. 2005).
Yang, G., et al., "An orally bioavailable antipoxvirus compound (ST-246) inhibits extracellular virus formation and protects mice from lethal orthopoxvirus Challenge," *J. Virol.*, 79(20):13139-13149 (Oct. 2005).
Quenelle, Debra C., et al., "Synergistic Efficacy of the Combination of ST-246 with CMX001 against Orthopoxviruses," Antimicrobial Agents and Chemotherapy, Nov. 2007, p. 4118-4127, vol. 51, No. 11.
Smee et al. "Characterization and Treatment of Cidofovir-Resistant Vaccinia (WR Strain) Virus Infections in Cell Culture and in Mice." *Antiviral Chem. Chemother*. 16.3(2005):203-211.
Tam. "Individual Variation in First-Pass Metabolism." *Clin. Pharmacokinet*. 25.4(1993):300 328.
Wawazonek et al. "Preparation of Long Chain Alkyl Hydroperoxides." *J. Org. Chem*. 25.4(196):621-623.
"Vistide Drug Description." Revised Apr. 12, 2009.
Hanlon et al. "A Recombinant Vaccinia-Rabies Virus in the Immunocompromised Host: Oral Innocuity, Progressive Parental Infection, and Therapeutics." *Vaccine*. 15.2(1997):140-148.
Lederman. "Progressive Vaccinia in a Military Smallpox Vaccinee— United States 2009." *Center for Disease Control*. May 19, 2009. Web. Retrieved Jan. 1, 2013. http://www.cdc.gov/mmwr/preview/mmwrhtml/mm58e0519a1.html.
Painter et al. "CMX001: Anti-Smallpox Agent Anti-Cytomegalovirus Agent Viral Polymerase Inhibitor." *Drugs Future*. 33.8(2008):655-661.

"Creating Orally Available Medicines from Bioactive Molecules." *Presentation at Big 2004 Annual International Convention*. (Jun. 7, 2004).
Aldern et al. "Increased Antiviral Activity of 1-O-Hexadecyloxypropyl-[2-14C]Cidofovir in MRC-5 Human Lung Fibroblasts is Explained by Unique Cellular Uptake and Metabolism." *Mol. Pharmacol*. 63.3(2003):678-681.
Andrei et al. "Activities of Various Compounds against Murine and Primate Polyomaviruses." *Antimicrob. Agents Chemother*. 41.3(1997):587-593.
Annaert et al. "In Vitro, Ex Vivo, and In Situ Intestinal Absorption Characteristics of the Antiviral Ester Prodrug Adefovir Dipivoxil." *J. Pharm. Sci*. 89.8(2000):1054-1062.
Balzarini et al. "Antiretrovirus Activity of a Novel Class of Acyclic Pyrimidine Nucleoside Phosphonates." *Antimicrob. Agents Chemother*. 45.7(2002):2185-2193.
Bartlett et sl. "Phase I Trial of Doxrubicin with Cyclosporine as a Modulator of Multidrug Resistance." *J. Clin. Oncol*. 12.4(1994):835-842.
Beadle et al. "Alkoxyalkyl Esters of Cidofovir and Cyclic Cidofovir Exhibit Mutiple-Log Enhancement of Antiviral Activity Against Cytomegalogivrus and Herpes Virus Replication In Vitro." *Antimicrob Agents Chemother*. 46.8(2002):2381-2386.
Bidanset et al. "Oral Activity of Ether Lipid Ester Prodrugs of Cidofovir Against Experimental Human Cytomegalovirus Infection." *J. Infect. Dis*. 190.3(2004):499-503.
Biron. "Antiviral Drugs for Cytomegalovirus Diseases." *Antiviral Res*. 71(2006):154-163.
Bray et al. "Antiviral Prophaylaxis of Smallpox." *J. Antimicrob. Chemother*. 54.1(2004):1-5.
Buller et al. "Efficacy of Oral Active Ether Lipid Analogs of Cidofovir in a Lethal Mousepox Model." *Virol*. 318.2(2004):474-481.
Ciesla et al. "Esterification of Cidofovir with Alkoxyalkanols Increases Oral Bioavailability and Diminishes Drug Accumulation in Kidney." *Antiviral Res*. 59.3(2003):163-171.
Connelly et al. "Mechanism of Uptake of the Phosphonate Analog (S)-1-(3-hydroxy-2-phosphonylmethoxy-propyl)Cytosine (HPMPC) in Vero Cells." *Biochem. Pharma*. 46.6(1993):1053-1057.
Dal Pozzo et al. "In Vitro Evaluation of the Anti-orf Virus Activity of Alkoxyalkyl Esters of CDV, cCDV and (S)-HPMPA." *Antiviral Res*. 75(2007):52-57.
De Clercq et al. "Therapeutic Potential of Nucleoside/Nucleotide Analogues Against Poxvirus Infections." *Rev. Med. Virol*. 14.5(2004):289-300.
De Clercq. "Antiviral Drugs in Current Clinical Use." *J. Virol*. 30.2(2004):115-133.
De Clercq. "Clinical Potential of the Acyclic Nucleoside Phosphonates Cidofovir, Adefovir, and Tenofovir in Treatment of DNA Virus and Retrovirus Infections." *Clin. Microbiol. Rev*. 16.4(2003):569-596.
De Clercq. "The Acyclic Nucleoside Phosphonates from Inception to Clinical Use: Historical Perspective." *Antiviral Res*. 75(2007):1-13.
De Clercq. "Vaccinia Virus Inhibitors as a Paradigm for the Chemotherapy of Poxvirus Infections." *Clin. Microbiol. Rev*. 14.2(2001):382-397.
Denes et al. "Main Adult Herpes Virus Infections of the CNS." *Anti-Infective Therapy*. 3.4(2005):663-678.
Fardis et al. "Case Study: Tenofovir Disoproxil Fumarate: An Oral Prodrug of Tenofovir." vol. V: *Prodrugs: Challenges and Rewards Part 1. Biotechnology, Pharmaceutical Aspects*. 5.20(2007):649-657.
Fisher et al. "Phase I Trial of Etoposidee with the Cyclosporine 5DZ PSC 833, a Modulator of Multidrug Resistance (MDR)." *Proc. Am Soc. Clin. Oncol*. 12(1994):143 (Abstract #368).
Gauvry et al. "Dealkylation of Dialkyl Phosphonates with Boron Tribromide." *Synthesis*. 4(2001):553-554.
Hammond et al. "Alkylglycerol Prodrugs of Phosphonoformate are Potent In Vitro Inhibitors of Nucleoside-Resistant Human Immunodeficiency Virus Type 1 and Select for Resistance Mutations that Suppress Zidovudine Resistance." *Antimicrob. Agents Chemother*. 45.6(2001):1621-1628.

(56) References Cited

OTHER PUBLICATIONS

Hartline et al. "Ether Lipid-Ester Prodrugs of Acyclic Nucleoside Phosphonates: Activity Against Adenovirus Replication In Vitro." *J. Infect. Dis.* 191.3(2005):396-399.
Held et al. "Treatment of BK Virus-Associated Hemorrhagic Cystitis and Simultaneous CMV Reactivation with Cidofovir." *Bone Marrow Transplant.* 26(2000):347-350.
Hillenkamp et al. "Topical Treatment of Acute Adenoviral Keratoconjunctivitis With 0.2% Cidofovir and 1% Cyclosporine." *Arch. Ophthalmol.* 119.10(2001):1487-1491.
Hockova et al. "5-Substituted-2,4-diamino-6-[2-(phosphonomethoxy)ethoxy]pyrimidines-Acyclic Nucleoside Phosphonate Analogues with Antiviral Activity." *J. Med. Chem.* 46.23(2003):5064-5073.
Holy et al. "6-[2-(Phosphonomethoxy)alkoxy]pyrimidines wth Antiviral Activity." *J. Med. Chem.* 45.9(2002):1918-1929.
Holy et al. "Structure-Antiviral Activity Relationship in the Series of Pyrimidine and Purine N[2(2-Phosphonomethoxy)ethyl] Nucleotide Analogues." *J. Med. Chem.* 42.12(1999):2064-2086.
Holy. "Phosphonomethoxyalkyl Analogs of Nucleotides." *Curr. Pharma Des.* 9.31(2003):2567-2592.
Holy. "Simple Method for Cleavage of Phosphonic Acid Diesters to Monoesters." *Synthesis.*4(1998):381-385.
Hostetler et al. "Enhanced Antiproliferative Effects of Alkozyalkyl Eseters of Cidofovir in Human Cervical Cancers Cells in vitro." *Mol. Cancer Ther.* 5.1(2005):156-159.
Hostetler. "Alkoxyalkyl Prodrugs of Acyclic Nucleoside Phosphonates Enchance Oral Antiviral Activity and Reduce Toxicity: Current State of the Art." *Antiviral Research.* 82.2(2009):A84-A98.
Huggins et al. "Orally Active Ether Lipid Prodrugs of Cidofovir for the Treatment of Smallpox." *Antiviral Res.* 53(2002):A66. (Abstract #104).
Jacobson. "Treatment of Cytomegalovirus Retinitis in Patients with the Acquired Immunodeficiency Syndrome." *Drug Ther.* 337(1997):105-114.
Jasko et al. "A New Approach to Synthesis of 5'-)-phosphonomethyl Derivatives of Nucleosides and Their Analogues." *Bioorganicheskaya Khimiya.*20.1(1994):50-54.
Josephson et al. "Polyomavirus-Associated Nephropathy: Update on Antiviral Strategies." *Transpl. Infect. Dis.* 8(2006):95-101.
Keith et al. "Evaluation of Nucleoside Phosphonates and Their Analogs and Prodrugs for Inhibition of Orthopoxvirus Replication." *Antimicrob Agents Chemother.* 47.7(2003):2193-2198.
Kern et al. "Oral Treatment of Murine Cytomegalovirus Infections with Ether Lipid Esters of Cidofovir." *Antimicrob Agents Chemother.* 48.9(2004):3516-3522.
Kern. "Pivotal Role of Animal Models in the Development of New Therapies for Cytomegalovirus Infections." *Antiviral Res.* 71(2006):164-171.
Kini et al. "Alkoxy Propane Prodrugs of Foscarnet: Effect of Alkyl Chain Length on In Vitro Antiviral Activity in Cells Infected with HIV-1, HSV-1 and HCMV." *Antiviral Res.* 36.1(1997):43-53.
Kornbluth et al. "Mutations in the E9L Polymerase Gene of Cidofovir-Resistant Vaccinia Virus Strain WR are Associated with the Drug Resistance Phenotype." *Antimicrob. Agents Chemother.* 50.12(2006):4038-4043.
Lebeau et al. "Activities of Alkoxyalkyl Esters of Cidofovir (CDV), Cyclic CDV, and (S)-9-(3-Hydroxy-2-Phosphonylmethoxypropyl)Adenine Against Orthopoxviruses in Cell Monolayers and in Organotypic Cultures." *Antimicrob. Agents Chemother.* 50.7(2006):2525-2529.
Lu et al. "Intraocular Properties of Hexadecyloxypropyl-Cyclic-Cidofovir in Guinea Pigs." *J. Ocul. Pharmacol. Ther.* 21.3(2005):205-209.
Lum et al. "Alteration of Etoposide Pharmacokinetics and Pharmacodynamics by Cyclosproine in a Phase I Trial to Modulate Multidrug Resistanc." *J. Clin. Oncol.* 10.10(1992):1635 1642.
Lum et al. "MDR Expression in Normal Tissues." *Hematol. Oncol. Clin. No. Amer.* 9.2(1995):319-336.
Niemi et al. "Bisphosphonate Prodrugs: Synthesis and in Vitro Evaluation of Novel Acyloxyalkyl Esters of Clodronic Acid." *J. Med. Chem.* 42.24(1999):5053-5058.
Painter et al. "Biochemical and Mechanical Basis for the Activity of Nucleoside Analogue Inhibitors of HIV Reserve Transcriptase." *Curr. Topics Med. Chem.* 4.10(2004):1035-1044.
Painter et al. "Design and Development of Oral Drugs for the Prophylaxis and Treatment of Smallpox Infection." *Trends Biotechnol.* 22.8(2004):423-427.
Parker et al. "Efficacy of Therapeutic Intervention with an Oral Ether-Lipid Analogue of Cidofovir (CMX001) in a Lethal Mousepox Model." *Antiviral Res.* 77.1(2008):39-49.
Portilla et al. "Progressive Multifocal Leukoencphalopathy Treated with Cidofovir in HIV-Infected Patients Receiving Highly Active Anti-Retroviral" *J. Infect.* 41(2000):182-184.
Quenelle et al. "Oral Treatment of Cowpox and Vaccinia Virus Infections in Mice with Ether Lipid Esters of Cidofovir." *Antimicrob. Agents Chemother.* 48.2(2004):404-412.
Quenelle et al. "Oral Treatment of Cowpox and Vaccinia Virus Infections in Mice with Ether Lipid Esters of Cidofovir." *Antimicrob. Agents Chemother.* 48.2(2004):404-412. Erratum in: *Antimicrob. Agents Chemother.* 48.5(2004):1919.
Quimby et al. "Tetrasodium Carbonyldiphosphonate." *J. Org. Chem.* 32.12(1967):4111-4114.
Randhawa et al. "Ether Lipids Ester Derivatives of Cidofovir Inhibit Polyomavirus BK Replication In Vitro." *Antimicrob. Agents Chemother.* 50.4(2006):1564-1566.
Rogers. "A General Synthesis of Phosphonic Acid Dichlorides Using Oxalyl Chloride and DMF Catalysis." *Tetrahed. Lett.* 33.49(1992):7473-7474.
Saady et al. "Direct Esterification of Phosphonic Acid Salts Using the Mitsunobu Reaction." *Synlett.* 6(1995):643-644.
Schinkel et al. "Multidrug Resistance and the Role of P-glycoprotein Knockout Mice." *Eur. J. Cancer.* 31A.7-8(1995):1295-1298.
Singh et al. "Raltegravir is a Potent Inhibitor of XMRV, a Virus Implicated in Prostate Cancer and Chronic Fatigue Syndrome." *PLoS One.* 4.5(2010):e9948.
Smee et al. "A Review of Compounds Exhibiting Anti-Orthopoxvirus Activity in Animal Models." *Antiviral Res.* 57.1-2(2003):41-52.
Smee et al. "Characterization and Treatment of Cidofovir-Resistant Vaccinia (1NR Strain) Virus Infections in Cell Culture and in Mice." *Antiviral Chem. Chemother.* 16.3(2005):203-211.
Smee et al. "Effects of Four Antiviral Substances on Lethal Vaccinia Virus (IHD Strain) Respiratory Infections in Mice." *Int. J. Antimicrob. Agents.* 23.5(2004):430-437.
Tam. "Individual Variation in First-Pass Metabolism." *Clin. Pharmacokinet.* 25.4(1993):300-328.
Toth et al. "Hexadcyloxypropyl-Cidofovir, CMX001, Prevents Adenovirus-Induced Mortality in a Permissive, Immunosuppressed Animal Model." *PNAS.* 105.20(2008):7293-7297.
Wan et al. "Alkoxyalkyl Esters of Cidofovir and Cyclic Cidofovir: Effects of Alkyl Chain Length, Unsaturation, and Substitution on the in vitro Antiviral Activity in Cells Infected with HSV-1 and HCMV." *224th ACS National Meeting.* Boston, MA. Aug. 18-22, 2002. (Abstract #MEDI-30).
Wan et al. "Dimethylformamide as a Carbon Monoxide Source in Fast Palladium-Catalyzed Aminocarbonylations of Aryl Bromides." *J. Org. Chem.* 67.17(2002):6232-6235.
Wawazonek et al. "Preparation of Long Chain Alkyl Hydroperoxides." *J. Org. Chem.* 25.4(196):621-623, 1960.
Williams-Aziz et al. "Comparative Activities of Lipid Esters of Cidofovir and Cyclic Cidofovir Against Replication of Herpesviruses In Vitro." *Antimicrob. Agents Chemother.* 49(2005):3724-3733.

* cited by examiner

COMPOUNDS, COMPOSITIONS AND METHODS FOR THE TREATMENT OF POXVIRUS INFECTIONS

CROSS REFERENCE TO RELATED APPLICATIONS

This application claims the benefit of priority to U.S. Provisional Application No. 60/669,730, filed Apr. 8, 2005, the disclosure of which is incorporated herein by reference.

GOVERNMENT LICENSE RIGHTS

This invention was made with government support under Grant No. 5U01AI057233 awarded by the National Institutes of Health. The government has certain rights in the invention.

TECHNICAL FIELD

This invention is a method and composition for the treatment of poxvirus infections, such as orthopox virus infections, with combination therapies.

BACKGROUND

The threat of an intentional or unintentional spread of poxvirus infections to a vulnerable population has led to increased efforts to find safe, rapidly deployable treatments against such infections. Vaccination is now being offered to some healthcare workers and other first responders. Previously reported smallpox vaccine-associated adverse reactions, along with the unknown prevalence of risk factors among today's population has prompted the preparation of guidance for clinicians in evaluating and treating patients with smallpox vaccination complications. Following this guidance, the vaccine is not recommended for those with eczema and other exfoliative skin disorders, those with hereditary or acquired immunodeficiencies, or for pregnant women (Keith et al., Antimicrobial Agents and Chemotherapy, May 2004, p. 1869-1871). Also, the Centers for Disease Control issued a health advisory recommending as a precautionary measure that persons with known cardiac disease not be vaccinated at this time (CDC Health Advisory, Mar. 26, 2003).

Cidofovir (CDV) and cyclic CDV (cCDV) have been shown to be potent inhibitors of poxvirus, but are inactive when given orally. The synthesis of cidofovir is described in U.S. Pat. No. 5,142,051, issued Aug. 25, 1992. Enhanced activity over the parent compound has been observed using lipid prodrugs such as hexadecyloxypropyl (HDP) and octadecyloxyethyl (ODE) derivatives of CDV and cCDV (HDP-CDV, HDP-cCDV, ODE-CDV and ODE-cCDV). The synthesis of lipid prodrugs of CDV and cCDV is described, for example, in U.S. Pat. No. 6,716,825, issued Apr. 26, 2004. The antiviral activity of alkoxyalkyl and alkyl esters of cidofovir against human and murine cytomegalovirus is described in Wan et al., Antimicrobial Agents and Chemotherapy, 49:656-662 (2005).

Due to the seriousness of the disease, there is a need for new therapies in the event of a poxvirus outbreak or in the event of complications that may occur in the use of vaccination. There is a need for compositions and methods for effectively treating poxvirus infections.

Therefore, it is an object of the invention to provide new methods and compositions for the treatment of poxvirus.

SUMMARY OF THE INVENTION

The present invention provides methods for treating a poxvirus infection comprising administering a combination of cidofovir or cyclic cidofovir, or salts, esters or prodrugs thereof, and one or more additional anti-pox viral agents, as described below.

In one embodiment, pharmaceutically acceptable compositions are provided that include cidofovir, cyclic cidofovir, or salts, esters, or prodrugs thereof, and one or more other anti-poxvirus agents. The compositions may be administered to a host in need thereof in an effective amount for the treatment or prophylaxis of a host infected with a poxvirus.

The cidofovir or cyclic cidofovir, or salt, ester or prodrug thereof, and one or more additional anti-pox viral agent, can be administered to a host in need thereof in an effective amount for the treatment or prophylaxis of a host infected with a poxvirus, optionally in combination with a pharmaceutically acceptable carrier, together or sequentially. The compound and compositions are administered by any suitable means of administration, including but not limited to oral, parenteral, topical, intravenous, inhalation, transdermal or buccal.

In one embodiment, cidofovir or cyclic cidofovir is optionally in prodrug form, including but not limited to covalently linked to an alkylglycerol, alkylpropanediol, 1-S-alkylthioglycerol, alkoxyalkanol or alkylethanediol, or in a salt form, which is optionally present in a composition. The prodrug can be administered in an effective amount for the treatment or prophylaxis of a poxvirus infection, such as a smallpox infection.

Thus, in one embodiment, a composition is provided that includes CDV or cCDV, or its prodrug, and at least one other anti-poxvirus agent, wherein the composition can be administered in an effective amount for the treatment of a poxvirus infection, such as a smallpox infection. In one embodiment, the cidofovir prodrug is an alkoxyalkyl ester of cidofovir, such as an alkoxyalkanol ester of cidofovir. For example, the cidofovir prodrug may have the structure:

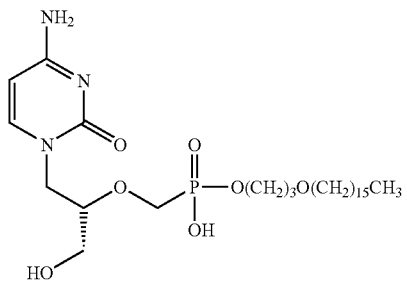

As examples, the compositions described herein can be used in methods for the prophylaxis or treatment of a host infected with an orthopox virus, such as variola major and minor, vaccinia, smallpox, cowpox, camelpox, mousepox, rabbitpox, and monkeypox.

Examples of useful anti-pox agents which can be administered in combination with cidofovir or cyclic cidofovir, or salts, esters or prodrugs thereof, include IMP dehydrogenase inhibitors, SAH hydrolase inhibitors, thymidylate synthase inhibitors, nucleoside analogues, acyclic nucleoside phosphonates, polyanionic substances, immunostimulatory agents and thiosemicarbazones.

In another embodiment, the one or more additional anti-pox agents is selected from ribarivirin, 5-iodo-2'-deoxyuridine, adenine arabinoside, trifluorothymidine, or an imidazoquinolinamine, such as imiquimod (Aldara) or resiquimod (R-848, S-28463). Other agents include 5-fluoro-dUrd, 5-bromo-dUrd and (E)-5-(2-bromovinyl)-dUrd or a nucleoside analog, for example 3'-C-methylcytidine and 3'-C-methyladenosine, 8-heptynyl-2'-deoxyadenosine, 8-alkyl-2'-deoxyadenosine, 8-alkenyl-2'-deoxyadenosine, 8-alkynyl-2'-deoxyadenosine; or an acyclic nucleoside phosphonate, for example adefovir.

The one or more additional anti-pox agent also may be a biologic, such as interferon (or an interferon-inducer, such as 4-iodo-antipyrine), pegylated interferon, interferon α, β, γ, ε, or τ, interferon alpha 2a, interferon alphacon-1, natural interferon, albuferon, interferon beta-1a, omega interferon, interferon alpha and interferon gamma-1b.

In another embodiment, the cidofovir or cyclic cidofovir, or salt, ester or prodrug thereof can be administered in combination or alternation with a biologic including immunomodulatory agents, such as colony stimulating factors, such as granulocyte macrophage colony-stimulating factor; an interleukin, such as interleukin-1α, interleukin-1β, interleukin-2, interleukin-3, interleukin-4, interleukin-5, interleukin-6, interleukin-7, interleukin-8, interleukin-10, interleukin-12; macrophage inflammatory proteins, such as macrophage inflammatory protein-1α, macrophage inflammatory protein-1β; and erythropoietin.

In one embodiment, the additional anti-pox agent is a compound which can be used to treat vaccinia vaccine complications, such as vaccinia immune globulin (VIG) or methisazone (Marboran). Other additional anti-pox agents include cytokines and immunostimulatory sequences ("ISSs"). ISSs are short DNA-like molecules, with distinct nucleotide sequences, that possess potent immunomodulatory properties which direct different immune system functions.

A variety of bioavailability enhancing agents may be administered or may be present in a pharmaceutical composition in an amount effective to enhance the bioavailability of the active agents described herein.

In one embodiment, the bioavailability enhancer is an inhibitor or substrate of an enzyme associated with drug biotransformation, such as one of the cytochrome P450 enzymes. In one embodiment, the enhancer is an antifungal, such as an imidazole antifungal, e.g., ketoconazole or troleandomycin; a macrolide, such as erythromycin; a calcium channel blocker, such as nifedipine; or a steroid, such as gestodene. Optionally, the compound is an inhibitor of cytochrome P450 3A (CYP3A), such as naringenin, found in grapefruit.

DETAILED DESCRIPTION OF THE INVENTION

Figure 1:
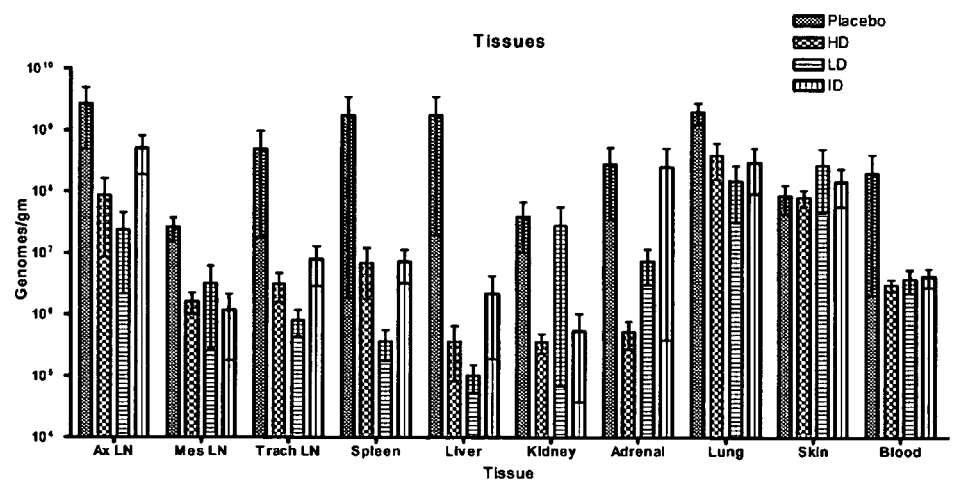
FIG. 1 shows the viral load of monkeypox titers in different types of tissue after drug administration.

The present invention provides methods for the treatment of a poxvirus infection, such as a smallpox infection, comprising administering an effective amount of cidofovir, cyclic cidofovir, or a pharmaceutically acceptable salt, ester, or prodrug thereof in combination or alternation with one or more anti-poxvirus agents. The additional anti-pox agent is, for example, a small molecule compound or a biologic such as an immunomodulatory polypeptide or nucleic acid.

Cidofovir Compounds

A variety of cidofovir compounds including cidofovir, cyclic cidofovir, or a salt, ester, or prodrug thereof can be used in the methods and compositions disclosed herein. Cidofovir or cyclic cidofovir may optionally be in the form of a prodrug wherein the phosphonate of cidofovir or cyclic cidofovir is covalently linked to a lipid group. Exemplary lipid groups include an alkylglycerol, alkylpropanediol, 1-S-alkylthioglycerol, alkoxyalkanol or alkylethanediol.

In one embodiment, the cidofovir prodrug compound has the structure:

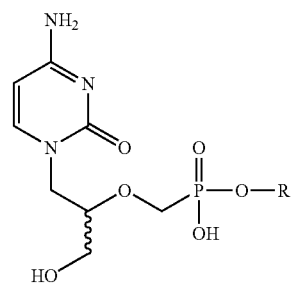

I wherein R is H; optionally substituted alkyl, e.g., $C_1$-$C_{30}$ alkyl; alkenyl, e.g., $C_2$-$C_{30}$ alkenyl; or alkynyl, e.g., $C_2$-$C_{30}$ alkynyl; acyl; mono- or di-phosphate; alkylglycerol, alkylpropanediol, 1-S-alkylthioglycerol, alkoxyalkanol or alkylethanediol. In one embodiment R is an alkoxyalkanol. For example, R is —$(CH_2)_m$—O—$(CH_2)_n$—$CH_3$ wherein, e.g., m is 1-5 and n is 1-25; or m is 2-4 and n is 10-25.

In another embodiment, the cidofovir prodrug compound has the following structure:

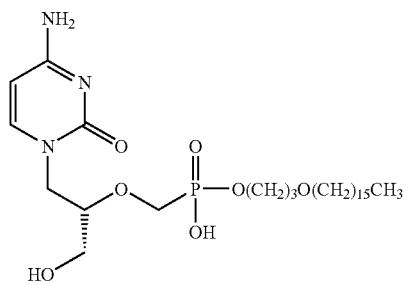

In one embodiment, a prodrug of cyclic cidofovir is provided.

In another embodiment, the prodrug compound has the following formula:

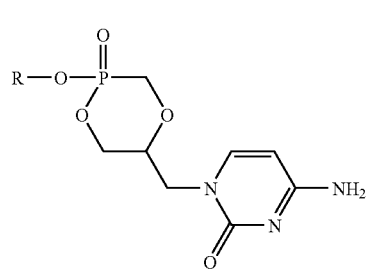

II wherein R is H; an optionally substituted alkyl, e.g., $C_1$-$C_{30}$ alkyl; alkenyl, e.g., $C_2$-$C_{30}$ alkenyl; alkynyl, e.g., $C_2$-$C_{30}$ alkynyl; acyl; mono- or di-phosphate; alkylglycerol, alkylpropanediol, 1-S-alkylthioglycerol, alkoxyalkanol or alkylethanediol. In one embodiment R is an alkoxyalkanol. R is for example —$(CH_2)_m$—O—$(CH_2)_n$—$CH_3$ wherein, for example, m is 1-5 and n is 1-25; or m is 2-4 and n is 10-25.

In another embodiment, the cidofovir or cyclic cidofovir prodrug compound is 1-O-octadecylpropanediol-3-cidofovir, 1-O-octadecylethanediol-2-cidofovir, 1-O-hexadecylpropanediol-3-cyclic cidofovir, 1-O-octadecylpropanediol-3-cyclic cidofovir, or 1-O-octadecylethanediol-2-cyclic cidofovir.

In one embodiment, the cidofovir or cyclic cidofovir prodrug compounds are hexadecyloxypropyl cidofovir, octadecyloxyethyl cidofovir, oleyloxypropyl cidofovir, octyloxypropyl cidofovir, dodecyloxypropyl cidofovir, oleyloxyethyl cidofovir, 1-O-octadecyl-2-O-benzyl-glyceryl cidofovir, tetradecyloxypropyl cidofovir, eicosyl cidofovir, docosyl cidofovir, hexadecyl cidofovir, hexadecyloxypropyl cyclic cidofovir, octadecyloxyethyl cyclic cidofovir, oleyloxypropyl cyclic cidofovir, octyloxypropyl cyclic cidofovir, dodecyloxypropyl cyclic cidofovir, oleyloxyethyl cyclic cidofovir, 1-O-octadecyl-2-O-benzyl-glyceryl cyclic cidofovir, tetradecyloxypropyl cyclic cidofovir, eicosyl cyclic cidofovir, docosyl cyclic cidofovir, or hexadecyl cyclic cidofovir.

A variety of lipid derivatives of cidofovir and cyclic cidofovir compounds can be used in the methods and compositions provided herein. In one embodiment, the cidofovir and cyclic cidofovir prodrugs have one of the following structures:

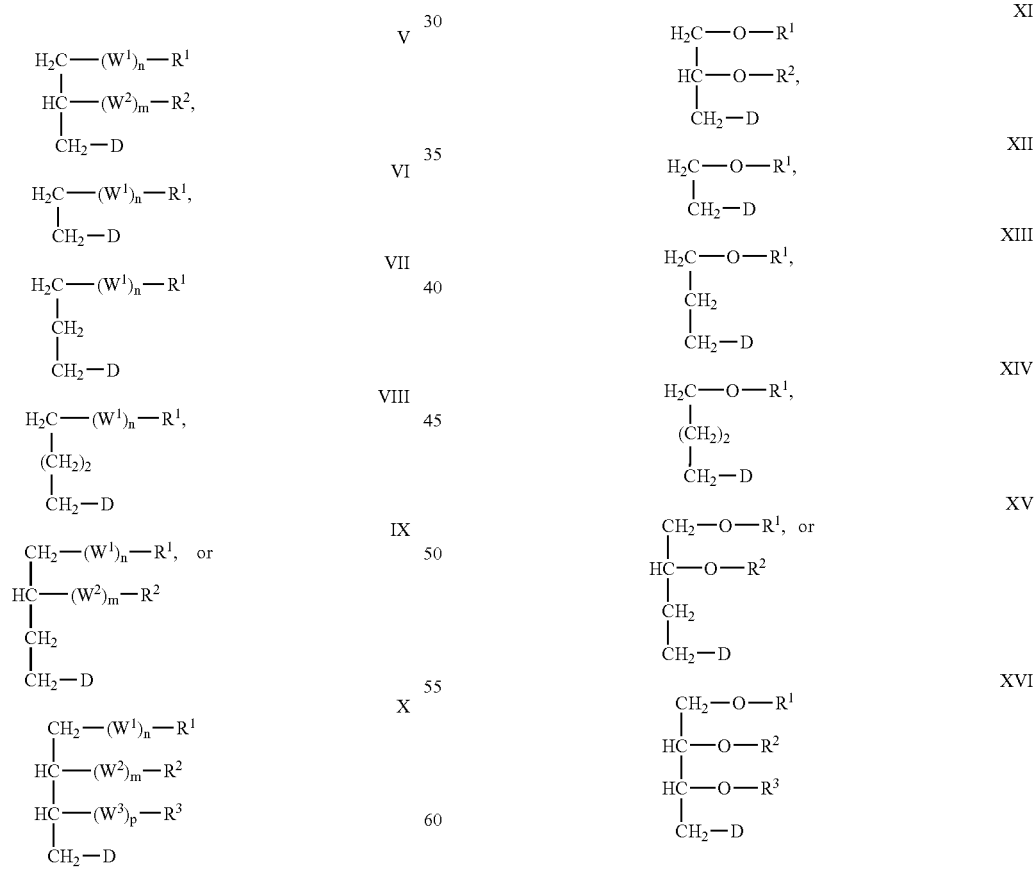

wherein $W^1$, $W^2$, and $W^3$ are each independently —O—, —S—, —SO—, —$SO_2$—, —O(C=O)—, —(C=O)O—, —NH(C=O)—, —(C=O)NH— or —NH—; and in one embodiment are each independently O, S, or —O(C=O)—;

n is 0 or 1; m is 0 or 1; p is 0 or 1

$R^1$ is an optionally substituted alkyl, alkenyl or alkynyl, e.g., $C_{1-30}$ alkyl, $C_{2-30}$ alkenyl, or alkynyl; or in one embodiment, $R^1$ is optionally $C_{8-30}$ alkyl, alkenyl or alkynyl, or $R^1$ is a $C_{8-24}$ alkyl, alkenyl or alkynyl (e.g., $C_{17}$, $C_{18}$, $C_{19}$, $C_{20}$, $C_{21}$, $C_{22}$, $C_{23}$, or $C_{24}$ alkyl, alkenyl, or alkynyl);

$R^2$ and $R^3$ are each independently an optionally substituted $C_{1-25}$ alkyl, $C_{2-25}$ alkenyl, or alkynyl; or in one embodiment, optionally $R^2$ and $R^3$ are each independently $C_{1-5}$ alkyl, $C_{2-5}$ alkenyl, or alkynyl (e.g., $C_1$, $C_2$, or $C_3$ alkyl, alkenyl or alkynyl; e.g., methyl, ethyl or propyl); or in another embodiment $CF_3$; or in another embodiment aryl, e.g., benzyl;

D is cidofovir or cyclic cidofovir linked, e.g. to an oxygen of the phosphonate group.

In one subembodiment of Formulas V-X:
$W^1$, $W^2$, and $W^3$ are each independently —O—, —S—, or —O(CO)—;

n is 0 or 1; m is 0 or 1; p is 0 or 1;

$R^1$ is optionally substituted $C_{18-24}$ alkyl or alkenyl (e.g., $C_{18}$, $C_{19}$, $C_{20}$, $C_{21}$, $C_{22}$, $C_{23}$, or $C_{24}$ alkyl);

$R^2$ and $R^3$ are each independently optionally substituted $C_{1-5}$ alkyl or $C_{2-5}$ alkenyl, benzyl, or $CF_3$; or are $C_1$, $C_2$, or $C_3$ alkyl, e.g., methyl or ethyl;

D is cidofovir or cyclic cidofovir, linked, e.g., via an oxygen of the phosphonate group.

In another subembodiment, the cidofovir or cyclic cidofovir prodrug has one of the following structures:

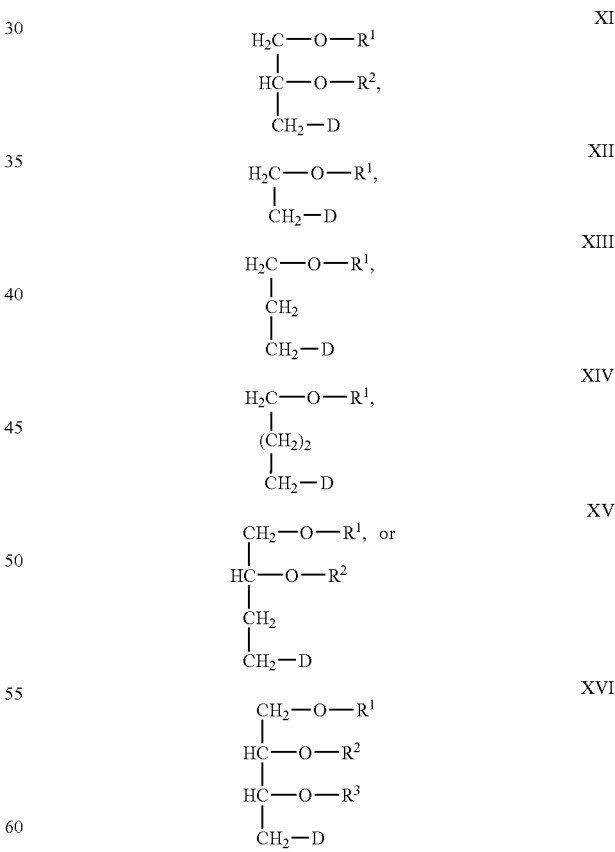

wherein $R^1$ is an optionally substituted $C_{8-24}$ alkyl, for example, $C_{18-24}$ alkyl (e.g., $C_{18}$, $C_{19}$, $C_{20}$, $C_{21}$, $C_{22}$, $C_{23}$, or $C_{24}$ alkyl);

$R^2$ and $R^3$ are independently $C_{1-5}$ alkyl, benzyl, or haloalkyl; or are e.g. methyl, ethyl or $CF_3$;

D is cidofovir or cyclic cidofovir, linked, e.g., via an oxygen of the phosphonate group.

Other prodrugs of cidofovir and cyclic cidofovir include (ethyl L-alaninyl) cyclic cidofovir, 2-(butyloxycarbonylphenyl) cyclic cidofovir, (phenethyl L-alaninyl) cyclic cidofovir, and (butyl L-alaninyl) cyclic cidofovir.

Optionally, two or more cidofovir and/or cyclic cidofovir prodrugs can be used in combination.

Combination Agents

A variety of anti-poxvirus compounds may be used with cidofovir, cyclic cidofovir, or its salts, esters or prodrugs thereof, in the methods and compositions provided herein. The second anti-pox agent can be a pharmaceutical compound, such as a nucleoside or nucleoside analogue, or in another embodiment may be a biologic, such as an immunomodulatory amino acid sequence or nucleic acid sequence.

Anti-poxvirus compounds that can be used include IMP dehydrogenase inhibitors, such as ribavirin; nucleoside analogues, such as 3'-C-methylcytidine; acyclic nucleoside phosphonates, such as adefovir; 2-, 6- and 8-alkylated adenosine analogues, such as 8-methyladenosine; thiosemicarbazones, such as N-methylisatin 3-thiosemicarbazone. See, e.g. Bray et al., *Antiviral Research* 58: 101-114 (2003).

Other anti-orthopox virus agents include polyanionic substances (e.g., polyacrylic acid, dextran sulfate, pentosan polysulfate, polyvinyl alcohol sulfate, and polyacrylic acid vinyl alcohol sulfate), N-phosphonoacetyl-L-aspartate, or $N_1$-isonicotinoyl-$N_2$-3-methyl-4-chlorobenzoylhydrazine.

The additional anti-orthopox agent is in a further embodiment, for example, a compound used to reduce potential pathology of smallpox vaccination, such as vaccinia immune globin, as well as methisazone, ribavarin, 5-iodo-2'-deoxyuridine, adenine arabinoside, trifluorothymidine, nucleoside analogs and interferon and interferon inducers (see, e.g., Bell et al., *Virology*, 325:425-431 (2004)).

The one or more additional anti-pox agent also may be a biologic such as interferon (or an interferon-inducer, such as 4-iodo-antipyrine), pegylated interferon, interferon α, β, γ, ε or τ, interferon alpha 2a, interferon alphacon-1, natural interferon, albuferon, interferon beta-1a, omega interferon, interferon alpha and interferon gamma-1b. Specific examples include PEG-INTRON® (peginterferon alpha-2b) and REBETOL® (Ribavirin, USP, Schering Corporation), INTRON® A (Interferon alpha-2b, recombinant, Schering Corporation), PEGASYS® (Roche's pegylated interferon alpha-2a), INFERGEN® (interferon alphacon-1) by InterMune, OMNIFERON® (natural interferon) by Viragen, ALBUFERON® by Human Genome Sciences, REBIF (interferon beta-1a) by Ares-Serono, Omega Interferon by Bio-Medicine, Oral Interferon Alpha by Amarillo Biosciences, interferon gamma, interferon tau, and Interferon gamma-1b by InterMune.

In another embodiment, the cidofovir or cyclic cidofovir, or salt, ester or prodrug thereof can be administered in combination or alternation with a biologic including immunomodulatory agents, such as colony stimulating factors, e.g. granulocyte macrophage colony-stimulating factor; an interleukin, such as interleukin-1α, interleukin-1β, interleukin-2, interleukin-3, interleukin-4, interleukin-5, interleukin-6, interleukin-7, interleukin-8, interleukin-10, interleukin-12; macrophage inflammatory proteins, such as macrophage inflammatory protein-1α, macrophage inflammatory protein-1β; and erythropoietin.

Other additional anti-pox agents include cytokines and immunostimulatory sequences ("ISSs"). ISSs are short DNA-like molecules, with distinct nucleotide sequences, that possess potent immunomodulatory properties which direct different immune system functions. ISSs which can be used are described, for example, in U.S. Pat. No. 6,194,388, issued Feb. 27, 2001; U.S. Pat. No. 6,207,646, issued Mar. 27, 2001; and U.S. Pat. No. 6,239,116, issued May 29, 2001, to Coley Pharmaceutical Group et al., the disclosures of which are incorporated herein by reference. Other ISSs that can be used are described in U.S. Pat. No. 6,589,940, issued Jul. 8, 2003; U.S. Pat. No. 6,562,798, issued May 13, 2003; and U.S. Pat. No. 6,225,292, issued May 1, 2001 to Dynavax Technologies Corp. et al, the disclosures of which are incorporated herein by reference. Other useful sequences are described in WO 96/02555; WO 98/18810; WO 98/40100; WO 99/51259; WO 00/06588; U.S. Pat. No. 6,218,371; WO 98/52581; WO 01/22990; WO 01/22972; as well as WO 98/55495; WO 97/28259; WO 98/16247; WO 00/21556; and WO 01/12223, the disclosures of which are incorporated herein by reference.

In another embodiment, the second anti-orthopox virus agent can be selected from analogs of adenosine-N(1)-oxide and analogs of 1-(benzyloxy) adenosine, such as 1-(3-methoxybenzyloxy) adenosine and 1-(4-methoxybenzyloxy) adenosine.

In another embodiment, the anti-orthopox virus agents include SAH hydrolase inhibitors, such as 5'-noraristeromycin, neplanocins A and C, carbocyclic 3-deaza-adenosine, 9-(2',3'-dihydroxycyclopenten-1-yl)adenine, DHCaA, $c^3$DHCeA, $c^3$DHCaA 6'-β-fluoro-aristeromycin, 5'-noraristeromycin and enantiomers and epimers thereof, 3-deaza-5'-noraristeromycin, 6'-C-methylneplanocin, 6'-homoneplanocin, 2-fluoroneplancin, 6'-iodo acetylenic Ado, and 3-deazaneplanocin.

In one embodiment, the second anti-poxvirus agent is selected from one or more of:
8-methyladenosine;
2-amino-7-[(1,3-dihydroxy-2-propoxy)methyl]purine (S2242);
(S)-9-(3-hydroxy-2-phosphonylmethoxypropyl)-2,6-diaminopurine ((S)-HPMPDAP);
(S)-9-(3-hydroxy-2-phosphonylmethoxypropyl)adenine (HPMPA);
cyclic HPMPA;
8-Aza-HPMPA;
adenine arabinoside;
adefovir (PMEA);
adefovir dipivoxil;
(S)-6-(3-hydroxy-2-phosphonylmethoxy-propyl)oxy-2,4-diaminopyrimidine ((S)-HPMPO-DAPy);
[(phosphonylmethoxy)ethyl]-N6-(cyclopropyl) DAP (PME-N6-(cyclopropyl) DAP);
PME-N6-(dimethyl)DAP;
PME-N6-(trifluoroethyl)DAP;
PMEA-N6-(2-propenyl)DAP;
bis(butyl L-alaninyl) adefovir;
bis(butyl L-alaninyl) PME-N6-(cyclopropyl)DAP;
(isopropyl L-alaninyl) phenyl PME-N6-(cyclopropyl)DAP;
novobiocin;
IMP dehydrogenase inhibitors (e.g., ribavirin, 5-ethynyl-1-beta-D-ribofuranosylimidazole-4-carboxamide (EICAR), FICAR, tiazofurin, and selenazole);
OMP decarboxylase inhibitors (e.g., pyrazofurin and 5'-deoxypyrazofurin);
CTP synthetase inhibitors (e.g., cyclopentenyl cytosine and carbodine);
thymidylate sythase inhibitors (e.g., 5-substituted 2'-deoxyuridines);
rifampin; and
3'-fluoro-3'-deoxyadenosine.

Optionally, the anti-orthopox virus agents disclosed herein are in the form of a prodrug, including but not limited to the prodrug structures disclosed above. The compounds are, for example, antiviral phosphonate prodrug compounds. Other, non-limiting examples of such prodrug structures are described in, for example, U.S. Pat. No. 5,223,263; U.S. Pat. No. 4,619,794; Japanese Patent 61-152694; U.S. Pat. No. 5,436,234; U.S. Pat. No. 5,411,947; U.S. Pat. No. 5,194,654; U.S. Pat. No. 5,463,092; U.S. Pat. No. 5,512,671; U.S. Pat. No. 5,484,911; U.S. Pat. No. 6,030,960; U.S. Pat. No. 5,962,437; U.S. Pat. No. 6,448,392; U.S. Pat. No. 5,770,584; U.S. Pat. No. 5,869,468; U.S. Pat. No. 5,84,228; U.S. Publication No. 2002/0082242; U.S. Publication No. 2004/0161398; U.S. Publication No. 2004/0259845; WO 98/38202; U.S. Pat. No. 5,696,277; U.S. Pat. No. 6,002,029; U.S. Pat. No. 5,744,592; U.S. Pat. No. 5,827,831; U.S. Pat. No. 5,817,638; and U.S. Pat. No. 6,252,060, the disclosures of which are incorporated herein by reference.

In one embodiment, the additional anti-pox agent is Siga-246 (or ST-246), or 4-trifluoromethyl-N-(3,3a,4,4a,5,5a,6,6a-octahydro-1,3-dioxo-4,6-ethenocycloprop[f]isoindol-2(1H)-yl)-benzamide. ST-246 is a potent and specific inhibitor of orthopoxvirus replication. It is active against multiple species of orthopoxviruses, including two strains of variola virus and a CDV-resistant cowpox virus variant (Yang, et al. 2005 J. Virol. 79:13139-13149). Resistance mapping studies indicate that ST-246 targets the cowpox virus V061 gene, which encodes a major envelope protein homologous to the vaccinia virus F13L gene product. The protein participates in the envelopment of intracellular mature virus (IMV) particles in virus-modified membranes derived from the trans-Golgi or early-endosome compartments to produce an egress-competent form of virus particle (Blasco, R., and B. Moss. 1991. J. Virol. 65:5910-5920). The structure is shown below.

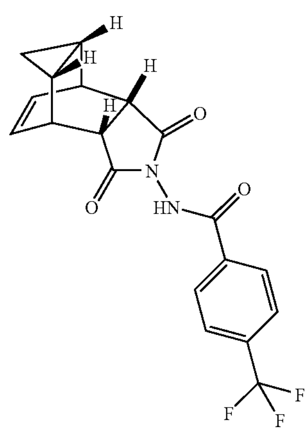 [SMILES: O=C(NN1C(=O)[C@@H]2C3C=CC([C@H]4C[C@@H]34)[C@@H]2C1=O)c1ccc(C(F)(F)F)cc1]

In another embodiment, the compounds provided herein are administered prior to or subsequent to the one or more additional active ingredients. In one embodiment, the cidofovir, cyclic cidofovir, or its salts, esters or prodrugs thereof, are administered serially or in combination with one or more anti-poxvirus agents.

Enhancers

Optionally, the anti-poxvirus agents and compositions provided herein may be administered with a bioavailability enhancing agent. A variety of bioavailability enhancing agents may be administered or may be present in a pharmaceutical composition in an amount effective to enhance the bioavailability of the anti-viral agent, e.g. by reducing degradation of a lipid group of a lipid prodrug.

"Drug bioavailability" refers to total amount of drug systemically available over time. Drug bioavailability can be increased by inhibiting drug biotransformation in the gut and/or by inhibiting active transport systems in the gut which decrease the net transport of drugs across gut epithelia, and/or by decreasing drug biotransformation in the liver. The compound causing increased drug bioavailability of the anti-viral drug is referred to herein as a bioenhancer.

Any bioassay that determines whether a given compound has the inhibition or binding characteristics required of a bioenhancer can be used to identify compounds that can be used.

In one embodiment, the bioavailability enhancer is an inhibitor or substrate of an enzyme associated with drug biotransformation, such as one of the cytochrome P450 enzymes. In one embodiment, the enhancer is an antifungal, such as an imidazole antifungal, e.g., ketoconazole or troleandomycin; a macrolide, such as erythromycin; a calcium channel blocker, such as nifedipine; or a steroids, such as gestodene. Optionally, the compound is an inhibitor of cytochrome P450 3A (CYP3A), such as naringenin, found in grapefruit.

Any agent that will effect the activity of an enzyme or receptor involved in drug biotransformation may be used. In one embodiment, the enzymes for which activity can be reduced are cytochrome P450 enzymes, and in particular the CYP3 family of enzymes.

In particular, the activity of the cytochrome P450 enzymes can be inhibited or the cytochrome P450 enzymes can be inactivated by drugs and environmental compounds. This includes competitive inhibition between substrates of the same cytochrome P450, inhibition by agents that bind sites on the cytochrome P450 other than the active site, and suicidal inactivation of the cytochrome P450 by reactive intermediates formed during the metabolism of an agent. For example, inhibitors can function by acting as a competitive, non-competitive, uncompetitive, mixed or irreversible inhibitor of CYP3A drug biotransformation. The inhibitor may also act by binding to the drug being protected, either by covalent bonding or by ionic or polar attractions.

The activity of CYP3A is defined as CYP3A catalyzed production of reaction product from CYP3A substrates. Substrates for CYP3A can be naturally occurring substrates or other components such as those listed in Table 1. In addition, some of the CYP3A inhibitors listed in Table 1 have been identified as substrates, as designated in the table. The catalytic activities of CYP3A, subject to inhibition, include dealkyase, oxidase, and hydrolase activities. In addition to the different catalytic activities of CYP3A, different forms of CYP3A exist with a range in molecular weight (for example, from 51 kD to 54 kD, as shown in Komori et al., J. Biochem. 1988, 104:912-16). The compounds listed in Table 1, in particular the inhibitors, can be used as enhancers in the methods and compositions described herein.

TABLE 1

| P450 3A substrates | P450 3A inhibitors |
|---|---|
| Antiarrhythmic | Antidiabetic |
| Amiodarone | Glibenclamide |
| Lidocaine | Tolbutamide |
| Quinidine | Benzodiazepine |
| Antiepileptic | Midazolam* |
| Etnosuximide | Calcium channel blocker |
| Zonisamide | Diluazem |

TABLE 1-continued

| P450 3A substrates | P450 3A inhibitors |
|---|---|
| Antidepressant | Felodipine |
|   Imipramine | Nicardipine |
|   Tianeptine | Nifedipine* |
| Benzodiazepine | Verapamil |
|   Clonazepam | Chemotherapeutic |
|   Diazepam |   Clotrimazole |
|   Triazolam |   Erythromycin* |
| Chemotherapeutics |   Fluconazole |
|   Dapsone |   Itraconazole |
|   Ifosfamide |   Josamycin |
| Environmental toxins |   Ketoconazole |
|   1.6-dinitropyrene |   Miconazole |
|   1-nitropyrene |   Midecamycin |
|   6-nitrochrysene |   Navelbine* |
|   Aflatoxin B1 |   Primaquine |
|   Benzo(a)pyrene |   Triacetylotendomycin* |
|   MOCA.sup.1 |   Vinblastine* |
|   PhIP.sup.2 |   Vincristine* |
| Immunosuppressant |   Vindesine* |
|   Cyclosporine | Flavanoids |
|   FK-506 |   Benzonavone |
|   Rapamycin |   Kaempferol |
| Narcotic |   Naringenin |
|   Alfentanil |   Quercetin |
|   Cocaine | Steroid hormone |
|   Codeine |   Cortisol* |
|   Ethyhmorphine |   Ethinylestradiol* |
| Steroid hormones |   Gestodene |
|   17ÿethynylestradiol |   Methylprednisolone |
|   Estradiol |   Norgestrel |
|   Flutamide |   Prednisolone |
|   Testosterone |   Prednisone |
| Miscellaneous |   Progesterone* |
|   1-tetrahydrocannabinol |   Tamoxifen* |
|   Acetaminophen |   Thiotestosterone |
|   Benzphetamine | Miscellaneous |
|   Dextromethorphan |   Bromocriptine |
|   Digitoxin |   DDEP |
|   Lovastatin |   Dihydroergotamine |
|   NOHA[3] |   Ergotamine |
|   Retinoic acid | |
|   Selegiline | |
|   Terfenadine | |

*Drugs marked * have also been identified as P450 3A substrates
1 MOCA: 4,4'-Methylenebis(2-Chloroaniline)
2 PhIP: 2amino-1-methyl-6-phenylimidazo[4,5-b]pyridine
3 NOHA: Nomega-hydroxy-L-arginine
4 DDEP: 3,5dicarbetoxy-2,6-dimethyl-4-ethyl-1,4-dihydropyridine In a particular embodiment the enhancer is an inhibitor of CYA enzymes such as paroxetine, fluoxetine, sertreline, fluvoxamine, nefazodone, venlafaxine, cimetidine, fluphenazine, haloperidol, perphenazine, thioridazine, diltiazem, metronidazole, troleandomyan, disulfiram, St. John's Wort, and omeprazole.

Exemplary enhancers include anti-viral protease inhibitors, e.g., indinavir, nelfnavir, ritonavir, saquinavir; and anti-fungal agents, e.g., fluconazole, itraconazole, ketoconazole, and miconazole.

Other enhancers include macrolides such as clarithromycin, erythromycin, nortriptyline, lignocaine, and anriodarone.

Other enhancers include 17-ethinyl-substituted steroids, for example, gestodene, ethinyl-estradiol, methoxsalen, and levonorgestrol.

Other enhancers include flavones such as quercetin and naringenin, and other compounds such as ethynyl estradiol, and prednisolone.

In one embodiment, the bioavailability enhancer is an inhibitor of P-glycoprotein (P-gp)-mediated membrane transport.

In another embodiment, the bioavailability enhancer is cyclosporine A, active blockers GF120918 (elacridar), LY335989 (zosuquidar), valspodar (PSC833), biricodar (VX 710), or R101933.

Tests for active enhancers that are available in the art may be used to select the appropriate compounds. For example, enzyme inhibition may be measured. In one embodiment, cultured cells of hepatocytes or enterocytes or freshly prepared cells from either liver or gut can be used to determine the ability of a compound to act as a CYP3A inhibitor. Various methods of gut epithelial cell isolation can be used such as the method of Watkins et al., J. Clin. Invest. 1985; 80:1029-36. Cultured cells, as described in Schmiedlin-Ren, P. et al., Biochem. Pharmacol. 1993; 46:905-918, can also be used. The production of CYP3A metabolites in cells can be measured using high pressure liquid chromatograph (HPLC) methods as described in the following section for microsome assays of CYP3A activity.

Microsomes from hepatocytes or enterocytes can also be used for CYP3A assays. Microsomes can be prepared from liver using conventional methods as discussed in Kronbach et al., Clin. Pharmacol. Ther 1988; 43:630-5. Alternatively, microsomes can be prepared from isolated enterocytes using the method of Watkins et al., J. Clin. Invest. 1987; 80:1029-1037. Microsomes from gut epithelial cells can also be prepared using calcium precipitation as described in Bonkovsky, H. L. et al., Gastroenterology 1985; 88:458-467. Microsomes can be incubated with drugs and the metabolites monitored as a function of time. In addition the levels of these enzymes in tissue samples can be measured using radioimmunoassays or western blots. Isolated microsomes can be used to determine inhibition of CYP3A drug biotransformation. Generally, the drug will be a substrate of CYP3A. The addition of the inhibitor will decrease the ability of CYP3A to catalyze drug metabolism. Inhibitors identified in this assay will be inhibitors of CYP3A function and diminish substrate catalysis. The production of metabolites can be monitored using high pressure liquid chromatography systems (HPLC) and identified based on retention times. CYP3A activity can also be assayed by calorimetrically measuring erythromycin demethylase activity as the production of formaldehyde as in Wrighton, et al., Mol. Pharmacol. 1985; 28:312-321 and Nash, T., Biochem. J. 1953; 55:416-421.

Methods of Treatment

Methods of treating, preventing, or ameliorating poxvirus infections are provided. In practicing the methods, effective amounts of cidofovir, cyclic cidofovir, or a salt, ester, or prodrug thereof and one or more other anti-orthopox virus agents, are administered sequentially or in combination. The compounds may be administered in any desired manner, e.g., via oral, rectal, nasal, topical (including buccal and sublingual), vaginal, or parenteral (including subcutaneous, intramuscular, subcutaneous, intravenous, intradermal, intraocular, intratracheal, intracisternal, intraperitoneal, and epidural) administration.

In one embodiment, the CDV, cCDV, or salt, ester, or prodrug thereof and one or more other anti-poxvirus agents, are administered in an effective amount for the treatment or prophylaxis of viral infections resulting from orthopox viruses, such as variola major and minor, vaccinia, molluscum contagiosum, orf (ecthyma contagiosum) smallpox, cowpox, camelpox, mousepox, rabbitpox, and monkeypox.

In one non-limiting embodiment, a therapeutically effective dosage to treat such an orthopox infection should produce a serum concentration of anti-viral agent of about 0.1 ng/ml to about 50-100 μg/ml. The pharmaceutical compositions, in another non-limiting embodiment, provide a dosage of from about 0.001 mg to about 2000 mg of compound per kilogram of body weight per day. Pharmaceutical dosage unit forms are prepared, in one non-limiting example, to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

In some embodiments, the CDV, cCDV, salt, ester or prodrug, and the biologic are administered by different routes of administration. Thus, one may be administered orally and one may be administered by any other route, such as intravenously. In some embodiments the cidofovir compound is administered orally in a suitable pharmaceutical carrier in combination or alternation with a biologic which is administered, for example, intravenously or parenterally.

The dosages given will depend on absorption, inactivation and excretion rates of the drug as well as other factors known to those skilled in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Synthesis of Antiviral Compounds

Antiviral compounds and prodrugs thereof may be synthesized using methods available in the art. As described in U.S. Pat. No. 6,716,825, the disclosure of which is incorporated herein by reference, the antiviral compounds provided herein can be prepared in a variety of ways, as generally depicted in Schemes I-II. The general phosphonate esterification methods described below are provided for illustrative purposes only and are not to be construed as limiting in any manner. Indeed, several methods have been developed for direct condensation of phosphonic acids with alcohols (see, for example, R. C. Larock, Comprehensive Organic Transformations, VCH, New York, 1989, p. 966 and references cited therein). Isolation and purification of the compounds and intermediates described in the examples can be effected, if desired, by any suitable separation or purification procedure such as, for example, filtration, extraction, crystallization, flash column chromatography, thin-layer chromatography, distillation or a combination of these procedures. Specific illustrations of suitable separation and isolation procedures are in the examples below. Other equivalent separation and isolation procedures can of course, also be used.

Scheme I illustrates a general synthesis of alkylglycerol or alkylpropanediol analogs of cidofovir, cyclic cidofovir, and other phosphonates. Treatment of 2,3-isopropylidene glycerol, 1, with NaH in dimethylformamide followed by reaction with an alkyl methanesulfonate yields the alkyl ether, 2. Removal of the isopropylidene group by treatment with acetic acid followed by reaction with trityl chloride in pyridine yields the intermediate 3. Alkylation of intermediate 3 with an alkyl halide results in compound 4. Removal of the trityl group with 80% aqueous acetic acid affords the O,O-dialkyl glycerol, 5. Bromination of compound 5 followed by reaction with the sodium salt of cyclic cidofovir or other phosphonate-containing nucleotide yields the desired phosphonate adduct, 7. Ring-opening of the cyclic adduct is accomplished by reaction with aqueous sodium hydroxide. The preferred propanediol species may be synthesized by substituting 1-O-alkylpropane-3-ol for compound 5 in Scheme I. The tenofovir and adefovir analogs may be synthesized by substituting these nucleotide phosphonates for cCDV in reaction (f) of Scheme I. Similarly, other nucleotide phosphonates may be formed in this manner.

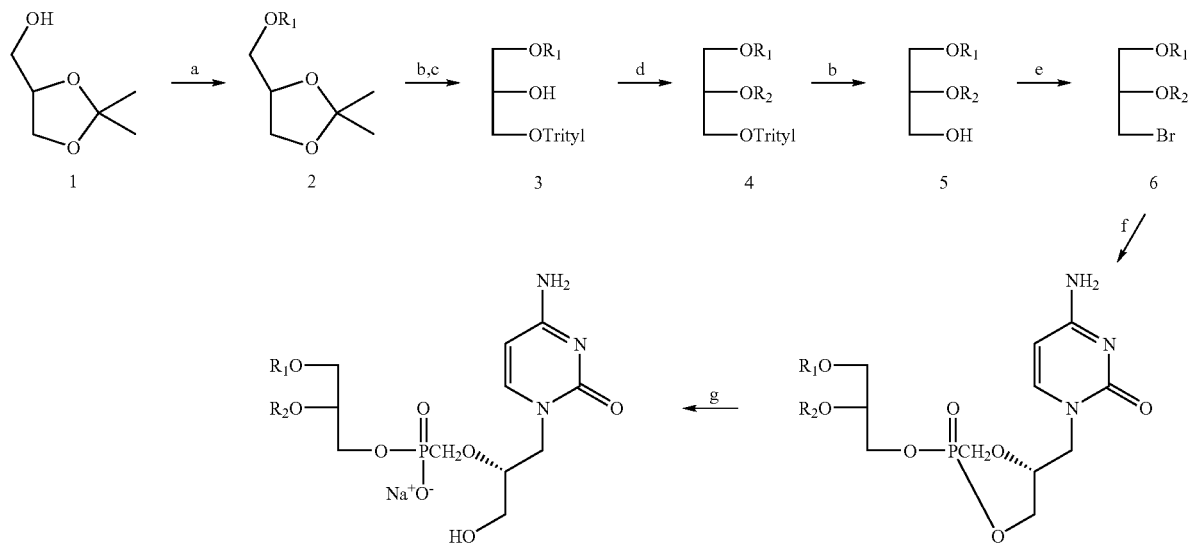

Reagents: a) NaH, R₁OSO₂Me, DMF; b) 80% aq acetic acid; c) Trityl chloride, pyridine; d) Nah, R₂-B₄, DMF; 30 CBr₄; triphenylphosphine, THF; f) cyclic cidofovir (DCMC salt), DMF; 0.5N NaOH Scheme II illustrates a general method for the synthesis of nucleotide phosphonates using 1-O-hexadecyloxypropyl-adefovir as the example. The nucleotide phosphonate (5 mmol) is suspended in dry pyridine and an alkoxyalkanol or alkylglycerol derivative (6 mmol) and 1,3-dicyclohexylcarbodiimide (DCC, 10 mmol) are added. The mixture is heated to reflux and stirred vigorously until the condensation reaction is complete as monitored by thin-layer chromatography. The mixture is then cooled and filtered. The filtrate is concentrated under reduced pressure and the residue is adsorbed on silica gel and purified by flash column chromatography (elution with approx. 9:1 dichloromethane/methanol) to yield the corresponding phosphonate monoester.

Scheme II

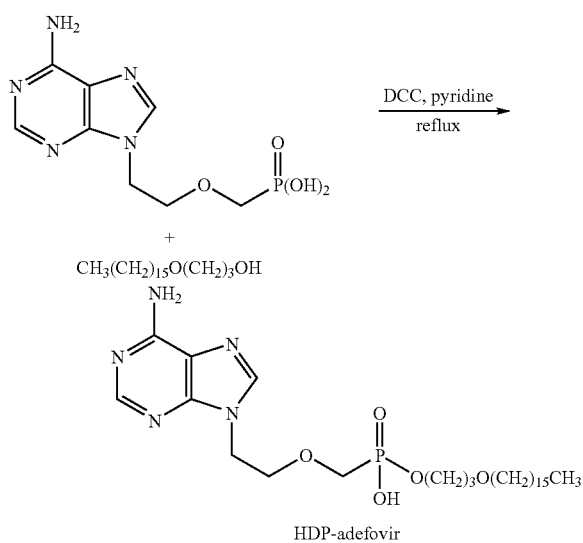

HDP-adefovir

Definitions

The term "alkyl", as used herein, unless otherwise specified, includes a saturated straight, branched, or cyclic, primary, secondary, or tertiary hydrocarbon, of, e.g., $C_{1-100}$ or e.g. $C_{1-22}$, and specifically includes methyl, ethyl, propyl, isopropyl, cyclopropyl, butyl, isobutyl, secbutyl, t-butyl, pentyl, cyclopentyl, isopentyl, neopentyl, hexyl, isohexyl, cyclohexyl, cyclohexylmethyl, heptyl, cycloheptyl, octyl, cyclooctyl, dodecyl, tridecyl, pentadecyl, icosyl, hemicosyl, and decosyl. The alkyl group may be optionally substituted with, e.g., halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

Whenever a range of carbon atoms is referred to, it includes independently and separately every member of the range. As a nonlimiting example, the term "$C_1$-$C_{10}$ alkyl" is considered to include, independently, each member of the group, such that, for example, $C_1$-$C_{10}$ alkyl includes straight, branched and where appropriate cyclic $C_1$, $C_2$, $C_3$, $C_4$, $C_5$, $C_6$, $C_7$, $C_8$, $C_9$ and $C_{10}$ alkyl functionalities.

The term "protected" as used herein and unless otherwise defined includes a group that is added to an atom such as an oxygen, nitrogen, or phosphorus atom to prevent its further reaction or for other purposes. A wide variety of oxygen and nitrogen protecting groups are known to those skilled in the art of organic synthesis.

The term "halo", as used herein, specifically includes to chloro, bromo, iodo, and fluoro.

The term "alkenyl" includes a straight, branched, or cyclic hydrocarbon of, for example, $C_{2-100}$, or $C_{2-22}$ with at least one double bond. Examples include, but are not limited to, vinyl, allyl, and methyl-vinyl. The alkenyl group can be optionally substituted in the same manner as described above for the alkyl groups.

The term "alkynyl" includes, for example, a $C_{2-100}$ or $C_{2-22}$ straight or branched hydrocarbon with at least one triple bond. The alkynyl group can be optionally substituted in the same manner as described above for the alkyl groups.

The term "alkoxy" includes a moiety of the structure —O-alkyl.

The term "acyl" includes a group of the formula R'C(O), wherein R' is a straight, branched, or cyclic, substituted or unsubstituted alkyl or aryl.

As used herein, "aryl" includes aromatic groups having in the range of 6 up to 14 carbon atoms and "substituted aryl" refers to aryl groups further bearing one or more substituents as set forth above.

As used herein, the term "bond" or "valence bond" includes a linkage between atoms consisting of an electron pair.

The term "host", as used herein, unless otherwise specified, includes mammals (e.g., cats, dogs, horses, mice, etc.), humans, or other organisms in need of treatment. The host is for example, a human or an animal, including without limitation, primates, including macaques, and baboons, as wells as chimpanzee, gorilla, and orangutan; ruminants, including sheep, goats, deer, and cattle, for example, cows, steers, bulls, and oxen; swine, including pigs; and poultry including chickens, turkeys, ducks, and geese.

The term "pharmaceutically acceptable salt" as used herein, unless otherwise specified, includes those salts which are, within the scope of sound medical judgment, suitable for use in contact with the tissues of hosts without undue toxicity, irritation, allergic response and the like, and are commensurate with a reasonable benefit/risk ratio and effective for their intended use. The salts can be prepared in situ during the final isolation and purification of one or more compounds of the composition, or separately by reacting the free base function with a suitable organic acid. Non-pharmaceutically acceptable acids and bases also find use herein, as for example, in the synthesis and/or purification of the compounds of interest. Nonlimiting examples of such salts are (a) acid addition salts formed with inorganic salts (for example hydrochloric acid, hydrobromic acid, sulfuric acid, phosphoric acid, nitric acid, and the like), and salts formed with organic salts such as acetic acid, oxalic acid, tartaric acid, succinic acid, ascorbic acid, benzoic acid, tannic acid, and the like; (b) base addition salts formed with metal cations such as zinc, calcium, magnesium, aluminum, sodium, potassium, copper, nickel and the like; (c) combinations of (a) and (b). Also included as "pharmaceutically acceptable salts" are amine salts.

The term "pharmaceutically acceptable esters" as used herein, unless otherwise specified, includes those esters of one or more compounds, which are, within the scope of sound medical judgment, suitable for use in contact with the tissues of hosts without undue toxicity, irritation, allergic response and the like, are commensurate with a reasonable benefit/risk ratio, and are effective for their intended use.

The term "pharmaceutically acceptable prodrug" includes a compound that is metabolized, for example, hydrolyzed or oxidized, in the host to form an active compound. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "enantiomerically enriched", as used herein, refers to a compound that is a mixture of enantiomers in which one enantiomer is present in excess, and preferably present to the extent of 95% or more, and more preferably 98% or more, including 100%.

The term "effective amount" includes an amount required for prevention, treatment, or amelioration of one or more of the symptoms of diseases or disorders provided herein.

It is to be understood that the compounds disclosed herein may contain chiral centers. Such chiral centers may be of either the (R) or (S) configuration, or may be a mixture thereof. Thus, the compounds provided herein may be enantiomerically pure, entantiomerically enriched, or be stereoisomeric or diastereomeric mixtures. It is understood that the disclosure of a compound herein encompasses any racemic, optically active, polymorphic, or steroisomeric form, or mixtures thereof, which preferably possesses the useful properties described herein, it being well known in the art how to prepare optically active forms and how to determine activity using the standard tests described herein, or using other similar tests which are well known in the art. Examples of methods that can be used to obtain optical isomers of the compounds include the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions, a technique whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis, a synthetic technique whereby the desired enantiomer is synthesized from an achiral precursor under conditions that produce assymetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations, a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Pharmaceutical Compositions

Pharmaceutical carriers suitable for administration of the compounds and biologics provided herein include any such carriers known to those skilled in the art to be suitable for the particular mode of administration including those described herein. The compounds may be formulated as the sole pharmaceutically active ingredient in the composition or may be combined with other active ingredients.

Compositions comprising the compounds disclosed herein may be suitable for oral, rectal, nasal, topical (including buccal and sublingual), vaginal, or parenteral (including subcutaneous, intramuscular, subcutaneous, intravenous, intradermal, intraocular, intratracheal, intracisternal, intraperitoneal, and epidural) administration.

The compositions may conveniently be presented in unit dosage form and may be prepared by conventional pharmaceutical techniques. Such techniques include the step of bringing into association one or more compositions provided herein and one or more pharmaceutical carriers or excipients.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives thereof may be mixed with one or more suitable pharmaceutical carriers. The compounds may be derivatized as the corresponding salts, esters, enol ethers or esters, acetals, ketals, orthoesters, hemiacetals, hemiketals, acids, bases, solvates, hydrates or prodrugs prior to formulation. The concentrations of the compounds in the compositions are effective for delivery of an amount, upon administration, that treats, prevents, or ameliorates one or more of the symptoms of the target disease or disorder. In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

Compositions suitable for oral administration may be presented as discrete units such as, but not limited to, tablets, caplets, pills or dragees capsules, or cachets, each containing a predetermined amount of one or more of the compositions; as a powder or granules; as a solution or a suspension in an aqueous liquid or a non-aqueous liquid; or as an oil-in-water liquid emulsion or a water-in-oil emulsion or as a bolus, etc.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents, preservatives, flavoring agents, and the like, for example, acetate, sodium citrate, cyclodextrine derivatives, sorbitan monolaurate, triethanolamine sodium acetate, triethanolamine oleate, and other such agents. Methods of preparing such dosage forms are known, or will be apparent, to those skilled in this art; for example, see Remington's Pharmaceutical Sciences, Mack Publishing Company, Easton, Pa., 15th Edition, 1975.

Compositions of the present invention suitable for topical administration in the mouth include for example, lozenges, having the ingredients in a flavored basis, usually sucrose and acacia or tragacanth; pastilles, having one or more of the compositions of the present invention in an inert basis such as gelatin and glycerin, or sucrose and acacia; and mouthwashes, having one or more of the compositions of the present invention administered in a suitable liquid carrier.

The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

Compositions suitable for topical administration to the skin may be presented as ointments, creams, gels, and pastes, having one or more of the compositions administered in a pharmaceutical acceptable carrier.

Compositions for rectal administration may be presented as a suppository with a suitable base comprising, for example, cocoa butter or a salicylate.

Compositions suitable for nasal administration, when the carrier is a solid, include a coarse powder having a particle size, for example, in the range of 20 to 500 microns which is administered in the manner in which snuff is taken, (i.e., by rapid inhalation through the nasal passage from a container of the powder held close up to the nose). When the carrier is a liquid (for example, a nasal spray or as nasal drops), one or more of the compositions can be admixed in an aqueous or oily solution, and inhaled or sprayed into the nasal passage.

Compositions suitable for vaginal administration may be presented as pessaries, tampons, creams, gels, pastes, foams or spray formulations containing one or more of the compositions and appropriate carriers.

Compositions suitable for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions which may include suspending agents and thickening agents. The compositions may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules, and tablets of the kind previously described above.

Pharmaceutical organic or inorganic solid or liquid carrier media suitable for enteral or parenteral administration can be used to fabricate the compositions. Gelatin, lactose, starch, magnesium stearate, talc, vegetable and animal fats and oils, gum, polyalkylene glycol, water, or other known carriers may all be suitable as carrier media.

Compositions may be used as the active ingredient in combination with one or more pharmaceutically acceptable carrier mediums and/or excipients. As used herein, "pharmaceutically acceptable carrier" includes any and all carriers, solvents, diluents, or other liquid vehicles, dispersion or suspension aids, surface active agents, isotonic agents, thickening or emulsifying agents, preservatives, solid binders, lubricants, adjuvants, vehicles, delivery systems, disintegrants, absorbents, preservatives, surfactants, colorants, flavorants, or sweeteners and the like, as suited to the particular dosage form desired.

Additionally, the compositions may be combined with pharmaceutically acceptable excipients, and, optionally, sustained-release matrices, such as biodegradable polymers, to form therapeutic compositions. A "pharmaceutically acceptable excipient" includes a non-toxic solid, semi-solid or liquid filler, diluent, encapsulating material or formulation auxiliary of any type.

It will be understood, however, that the total daily usage of the compositions will be decided by the attending physician within the scope of sound medical judgment. The specific therapeutically effective dose level for any particular host will depend upon a variety of factors, including for example, the disorder being treated and the severity of the disorder; activity of the specific composition employed; the specific composition employed, the age, body weight, general health, sex and diet of the patient; the time of administration; route of administration; rate of excretion of the specific compound employed; the duration of the treatment; drugs used in combination or coincidential with the specific composition employed; and like factors well known in the medical arts. For example, it is well within the skill of the art to start doses of the composition at levels lower than those required to achieve the desired therapeutic effect and to gradually increase the dosage until the desired effect is achieved.

Compositions are preferably formulated in dosage unit form for ease of administration and uniformity of dosage. "Dosage unit form" as used herein refers to a physically discrete unit of the composition appropriate for the host to be treated. Each dosage should contain the quantity of composition calculated to produce the desired therapeutic affect either as such, or in association with the selected pharmaceutical carrier medium.

Exemplary unit dosage formulations are those containing a daily dose or unit, daily sub-dose, or an appropriate fraction thereof, of the administered ingredient. The dosage will depend on host factors such as weight, age, surface area, metabolism, tissue distribution, absorption rate and excretion rate. Exemplary systemic dosages for all of the herein described conditions are those ranging from 0.01 mg/kg to 2000 mg/kg of body weight per day as a single daily dose or divided daily doses. Typical dosages for topical application are those ranging from 0.001 to 100% by weight of the active compound.

The therapeutically effective dose level will depend on many factors as noted above. In addition, it is well within the skill of the art to start doses of the composition at relatively low levels, and increase the dosage until the desired effect is achieved.

Compositions comprising a compound disclosed herein may be used with a sustained-release matrix, which can be made of materials, usually polymers, which are degradable by enzymatic or acid-based hydrolysis or by dissolution. Once inserted into the body, the matrix is acted upon by enzymes and body fluids. A sustained-release matrix for example is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho) esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (copolymers of lactic acid and glycolic acid).

The compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The liposome can contain, in addition to one or more compositions of the present invention, stabilizers, preservatives, excipients, and the like. Examples of lipids are the phospholipids and the phosphatidyl cholines (lecithins), both natural and synthetic. Methods to form liposomes are known in the art.

The compounds may be formulated as aerosols for application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

Compositions comprising the compounds disclosed herein may be used in combination with other compositions and/or procedures for the treatment of the conditions described above.

The invention will be further understood from the following non-limiting examples.

EXAMPLES

Example 1

As Described in U.S. Pat. No. 6,716,825

Synthesis of the Hexadecyloxypropyl, Octadecyloxypropyl, Octadecyloxyethyl and Hexadecyl Esters of Cyclic Cidofovir To a stirred suspension of cidofovir (1.0 g, 3.17 mmol) in N,N-DMF (25 mL) was added N,N-dicyclohexyl-4-morpholine carboxamidine (DCMC, 1.0 g, 3.5 mmol). The mixture was stirred overnight to dissolve the cidofovir. This clear solution was then charged to an addition funnel and slowly added (30 min.) to a stirred, hot pyridine solution (25 mL, 60° C.) of 1,3-dicyclohexyl carbodiimide (1.64 g, 7.9 mmol). This reaction mixture was stirred at 100° C. for 16 h then cooled to room temperature, and the solvent was removed under reduced pressure. The residue was adsorbed on silica gel and purified by flash column chromatography using gradient elution ($CH_2Cl_2$+MeOH). The UV active product was finally eluted with 5:5:1 $CH_2Cl_2$/MeOH/$H_2O$. Evaporation of the solvent gave 860 mg of a white solid. The $^1H$ and $^{31}P$ NMR spectrum showed this to be the DCMC salt of cyclic cidofovir (yield=44%).

To a solution of cyclic cidofovir (DCMC salt) (0.5 g, 0.8 mmol) in dry DMF (35 mL) was added 1-bromo-3-hexadecyloxypropane (1.45 g, 4 mmol) and the mixture was stirred and heated at 80° C. for 6 h. The solution was then concentrated in vacuo and the residue adsorbed on silica gel and purified by flash column chromatography using gradient elution ($CH_2Cl_2$+EtOH). The alkylated product was eluted with 90:10 $CH_2Cl_2$/EtOH. The fractions containing pure product were evaporated to yield 260 mg HDP-cyclic cidofovir (55% yield).

To a solution of cyclic cidofovir (DCMC salt) (1.0 g, 3.7 mmol) in dry DMF (35 mL) was added 1-bromo-3-octadecyloxypropane (2.82 g, 7.2 mmol) and the mixture was stirred and heated at 85° C. for 5 h. The solution was then concentrated in vacuo and the residue adsorbed on silica gel and purified by flash column chromatography using gradient elution ($CH_2Cl_2$+MeOH). The alkylated product was eluted with 9:1 $CH_2Cl_2$/MeOH. The fractions containing pure product were evaporated to yield 450 mg ODP-cyclic cidofovir.

To a solution of cCDV (DCMC salt) (1.0 g, 3.7 mmol) in dry DMF (35 mL) was added 1-bromo-3-octadecyloxyethane (3.0 g, 7.9 mmol) and the mixture was stirred and heated at 80° C. for 4 h. The solution was then concentrated in vacuo and the residue adsorbed on silica gel and purified by flash column chromatography using gradient elution ($CH_2Cl_2$+ MeOH). The alkylated product was eluted with 9:1 $CH_2Cl_2$/

MeOH. The fractions containing pure product were evaporated to yield 320 mg octadecyloxyethyl-cCDV.

To a solution of cyclic cidofovir (DCMC salt) (0.5 g, 0.8 mmol) in dry DMF (35 mL) was added 1-bromo-hexadecane (1.2 g, 4 mmol) and the mixture was stirred and heated at 80° C. for 6 h. The solution was then concentrated in vacuo and the residue adsorbed on silica gel and purified by flash column chromatography using gradient elution ($CH_2Cl_2$+MeOH). The alkylated product was eluted with 9:1 $CH_2Cl_2$/MeOH. The fractions containing pure product were evaporated to yield 160 mg hexadecyl-cCDV.

Example 2

As Described in U.S. Pat. No. 6,716,825

Synthesis of the Hexadecyloxypropyl, Octadecyloxypropyl, Octadecyloxyethyl and Hexadecyl Esters of Cidofovir Hexadecyloxypropyl-cyclic CDV from above was dissolved in 0.5M NaOH and stirred at room temp for 1.5 h. 50% aqueous acetic was then added dropwise to adjust the pH to about 9. The precipitated HDP-CDV was isolated by filtration, rinsed with water and dried, then recrystallized (3:1 p-dioxane/water) to give HDP-CDV.

Similarly, the octadecyloxypropyl-, octadecyloxyethyl- and hexadecyl-cCDV esters were hydrolyzed using 0.5M NaOH and purified to give the corresponding cidofovir diesters.

Example 3

As Described in U.S. Pat. No. 6,716,825

Effect of HDP-cCDV on Poxvirus Replication, In Vitro

The activity of cidofovir (CDV), cyclic cidofovir (cCDV), and 1-O-hexadecylpropanediol-3-cCDV (HDP-cCDV) was tested for antiviral activity in human foreskin fibroblasts infected with vaccinia virus or cowpox virus by measuring the dose dependent reduction in cytopathic effect (CPE). Preliminary vaccinia and cowpox $EC_{50}$ values were determined in a CPE reduction assay in human foreskin fibroblast (HFF) cells. The data thus obtained is shown in Table 3.

TABLE 3

| Drug | Vaccinia $EC_{50}$, μM | Cowpox, $EC_{50}$, μM | HFF Cells, $CC_{50}$, μM |
|---|---|---|---|
| CDV | 1.80 | 2.10 | 89.8 |
| Cyclic CDV | 0.97 | 0.72 | >100 |
| HDP-cCDV | 0.11 | <0.03 | >100 |
| Control lipid | >100 | >100 | >100 |

As shown in Table 3, HDP-cCDV was highly active against vaccinia virus with an $IC_{50}$ value of 0.11 μM versus 0.97 and 1.8 μM for cCDV and CDV, respectively. In cowpox infected cells HDP-cCDV was extremely effective with an $IC_{50}$ of <0.03 μM versus 0.72 and 2.1 for cCDV and CDV, respectively.

Poxvirus Antiviral Cytopathic Effect (CPE) Assay:

At each drug concentration, three wells containing Vero cells were infected with 1000 pfu/well of orthopoxvirus and three others remained uninfected for toxicity determination. Plates were examined and stained after the virus-infected, untreated cells showed 4+CPE. Neutral red was added to the medium and CPE was assessed by neutral red uptake at 540 nm. The 50% inhibitory ($EC_{50}$) and cytotoxic concentrations ($CC_{50}$) were determined from plots of the dose response. The results are shown in Table 4.

TABLE 4

| | | | $EC_{50}$ μM | | | |
|---|---|---|---|---|---|---|
| Compound | Vaccinia | Cowpox | Variola Major, Bangladesh | Variola Major, Yamada | Variola Minor Garcia | $CC_{50}$ μM |
| CDV | 2.2 | 3.8 | 100 | — | — | >100 |
| cCDV | — | — | 100 | — | — | >100 |
| HDP-CDV | <0.03 | <0.03 | 0.0015 | 0.0015 | 0.0006 | >0.1 |
| HDP-cCDV | 0.11 | <0.03 | >0.01 | — | — | >0.1 |

$EC_{50}$—50% effective concentration,
$CC_{50}$—50% cytotoxic concentration in Verocells;
selectivity index - $CC_{50}/EC_{50}$;
Results are the average of 3 determinations.

Example 4

Titer Study in Monkeys

Sixteen Cynomolgus Macaques were tested with 4 treatment groups of 4 animals each. The animals were inoculated with $5 \times 10^7$ PFU IV, Monkeypox virus, Zaire 79 strain. The animals were given placebos, or different dosage levels (TD: 35, 30, 20, 0 mg/kg), shown in FIG. 1 as HD, LD, ID and placebo respectively. FIG. 1 shows the viral load of monkeypox titers in different types of tissue after drug administration.

Example 5

Metabolic Stability Evaluation

Figure 2:
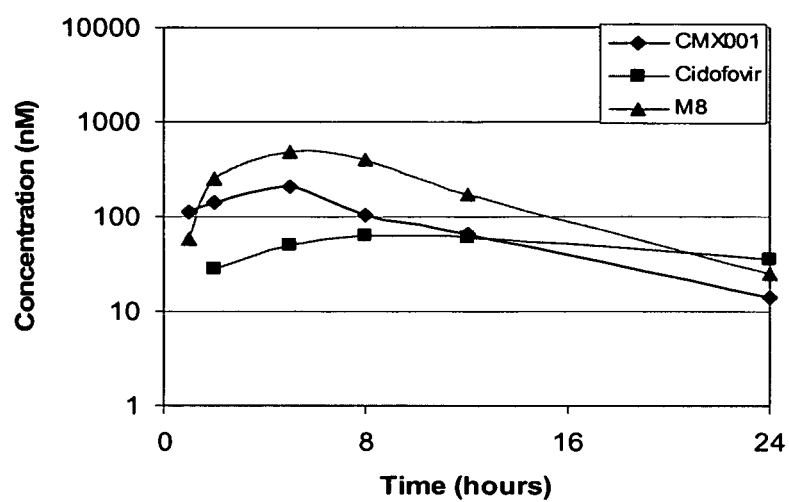
FIG. 2 illustrates the serum concentration of HDP-cidofovir, cidofovir released from HDP-cidofovir, and the metabolite M-8, which is an inactive metabolite of HDP-cidofovir, in mouse.

The serum concentration of HDP-cidofovir ("CMX-001"), cidofovir released from HDP-cidofovir, and the metabolite M-8, which is an inactive metabolite of HDP-cidofovir, in the mouse was evaluated, and the results are shown in FIG. 2 after a single oral dose.

What is claimed is:

1. A method for the treatment of a poxvirus infection comprising administering an effective amount of a prodrug of cidofovir having the structure:

or a pharmaceutically acceptable salt thereof, in combination or alternation with at least a second anti-pox virus agent to a host in need thereof, wherein the second anti-pox agent is Siga-246 (4-trifluoromethyl-N-(3,3a, 4,4a,5,5a,6,6a-octahydro-1,3-dioxo-4,6-ethenocycloprop[f]isoindol-2(1H)-yl)-benzamide), and the prodrug or a pharmaceutically acceptable salt thereof and the second anti-pox virus agent are each administered orally.

2. The method of claim 1 wherein the prodrug of cidofovir, or a pharmaceutically acceptable salt thereof and the second anti-pox virus agent are each administered in a pharmaceutically acceptable carrier.

3. The method of claim 1 wherein the prodrug of cidofovir, or a pharmaceutically acceptable salt thereof and the second anti-pox virus agent are administered in combination.

4. The method of claim 1 wherein the prodrug of cidofovir, or a pharmaceutically acceptable salt thereof and the second anti-pox virus agent are administered in alternation.

5. The method of claim 1, wherein the poxvirus is an orthopox virus selected from the group consisting of variola major and minor, vaccinia, smallpox, cowpox, camelpox, mousepox, rabbitpox, and monkeypox.

6. The method of claim 1, wherein the host is human.

7. The method of claim 1, wherein the poxvirus is smallpox virus.

8. The method of claim 1, wherein the poxvirus infection comprises more than one virus.

9. The method of claim 8, wherein the at least one virus is an orthopoxvirus.

10. The method of claim 8, wherein the at least one virus is selected from the group consisting of variola major and minor, vaccinia, smallpox, cowpox, camelpox, mousepox, rabbitpox, and monkeypox.

11. The method of claim 8, wherein the at least one virus is vaccinia virus or cowpox virus.

* * * * *